(12) United States Patent
Huffman et al.

(10) Patent No.: US 6,355,838 B1
(45) Date of Patent: Mar. 12, 2002

(54) REAGENTS FOR HEAT ACTIVATED POLYMER CROSSLINKING

(75) Inventors: Brian S. Huffman, Somerset, NJ (US); Rose Ann Schultz, Westford, MA (US); Peter J. Schlom, Somerville; James W. Nowicki, Hopewell, both of NJ (US); Ju-Ming Hung, Yardley, PA (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/243,199

(22) Filed: Feb. 2, 1999

(51) Int. Cl.[7] ............ C07C 235/14; C07C 233/57; C07C 233/00; C07C 235/00
(52) U.S. Cl. ............ 564/152; 560/156; 564/123; 564/193; 564/199
(58) Field of Search ............ 564/123, 152, 564/193, 199; 544/222; 560/156

(56) References Cited

U.S. PATENT DOCUMENTS

| | | | |
|---|---|---|---|
| 3,390,133 A | 6/1968 | Breslow | 525/332.5 |
| 3,390,204 A | 6/1968 | Breslow | 525/377 |
| 3,418,285 A | 12/1968 | Breslow | 525/326.9 |
| 3,448,063 A | 6/1969 | Breslow | 525/331.7 |
| 3,454,506 A | 7/1969 | Brack | 521/92 |
| 3,504,017 A | 3/1970 | Breslow | 560/168 |
| 3,526,218 A | 9/1970 | Reiss et al. | 128/2 |
| 3,526,236 A | 9/1970 | Osborne | 133/8 |
| 3,576,908 A | 4/1971 | Brack | 525/105 |
| 3,670,023 A | 6/1972 | Breslow | 562/804 |
| 3,681,299 A | 8/1972 | Bateman | 528/374 |
| 3,706,715 A | 12/1972 | Brack | 525/453 |
| 3,717,560 A | 2/1973 | Breslow | 204/159.18 |
| 3,754,877 A | 8/1973 | Klug | 44/7 B |
| 3,828,024 A | 8/1974 | Breslow | 548/962 |
| 3,832,399 A | 8/1974 | Breslow | 562/805 |
| 3,840,506 A | 10/1974 | Collette et al. | 525/375 |
| 3,878,220 A | 4/1975 | Breslow | 546/264 |
| 3,880,865 A | 4/1975 | Breslow | 546/140 |
| 3,897,395 A | 7/1975 | D'Alelio | 526/263 |
| 3,903,049 A | 9/1975 | Saltman et al. | 525/152 |
| 3,910,929 A | 10/1975 | Breslow | 546/133 |
| 3,917,698 A | 11/1975 | Breslow | 564/229 |
| 3,931,106 A | 1/1976 | Crosby et al. | 528/10 |
| 3,935,167 A | 1/1976 | Marvel et al. | 528/125 |
| 3,962,161 A | 6/1976 | Trapasso | 528/73 |
| 3,985,709 A | 10/1976 | Saltman et al. | 525/152 |
| 4,014,893 A | 3/1977 | Crosby et al. | 548/126 |
| 4,247,474 A | 1/1981 | Breslow | 558/299 |
| 5,021,507 A | 6/1991 | Stanley et al. | 525/127 |
| 5,123,951 A | * 6/1992 | See et al. | 504/127 |
| 5,290,908 A | 3/1994 | D'Alelio | 528/353 |
| 5,550,191 A | 8/1996 | Hung et al. | 525/92 C |
| 5,710,290 A | 1/1998 | Lysenko et al. | 549/513 |

FOREIGN PATENT DOCUMENTS

| | | |
|---|---|---|
| BE | 814889 A | 11/1974 |
| DE | 2547795 | 10/1974 |
| DE | 2422764 | 11/1974 |
| DE | 2547527 | 5/1976 |
| JP | 51000592 | 1/1976 |
| JP | 57012003 A2 | 1/1982 |
| WO | WO 87 05781 | 10/1987 |
| WO | WO 96/11229 | 4/1996 |
| WO | WO 97 03034 | 1/1997 |
| WO | WO 97/03142 | 1/1997 |

OTHER PUBLICATIONS

Leslie–Smith, Morag G. et al., "Divergent Behavior in the Isocyanate–Induced and Thermal Generation of Nitrile Oxide from Ethyl Nitroacetate", *Tetrahedron Lett.* (1994), 35 (49), 9251–4, XP002162593.

Shimizu, Tomio, et al., "Synthesis of Isoxzoline—3–carboxanilides and isoxazole–3–carboxanilides by thermolysis of .alpha–(methoxycarbonyl)–.alpha.–nitroa cetanilides in the presence of dipolarophiles", *Synthesis* (1996), (6), 488–90, XP002162592 compound 3a.

Landis et al., Polym. Prepr., Am. Chem. Soc., Div. Polym. Chem. (1974), 15(2), 533–6.

Brack, Karl, Def. Publ., U.S. Pat. Off.T, 24 pp., US 926001, Sep. 3, 1974.

Illarionova et al., Otkrytiya, Izobret. Prom. Obratsy, Tovarnye Znaki 1978, 55(36), 103.

Hayashi, M. et al., Nippon gomu Kyokaishi (1971), 44(11), 915–22.

Yoneda et al., Kogyo Kagaku Zasshi (1971), 74(8), 1701–6.

Hayashi et al., Nippon Gomu Kyokaishi (1970), 43(10), 807–17.

Hayashi et al., Nippon Gomu Kyokaishi (1970), 43(10), 818–25.

Hayashi et al., Nippon Gomu Kyokaishi (1970), 43(5), 358–62.

Hayashi et al., Nippon Gomu Kyokaishi (1970), 43(5), 363–8.

Hayashi et al., Nippon Gomu Kyokaishi (1970), 43(4), 313–18.

Nishita et al., Nippon Gomu Kyokaishi (1970), 43(4), 307–12.

DePasquale et al., Sci. Tech. Aerosp. Rep. 1983, 21(1), Abstr. No. N83–10195.

Emyashev et al., Vysokomol. Soedin., Ser. B (1979), 21(10), 728–31.

Samyn et al., J. Polym. Sci., Polym. Chem. Ed. (1975), 13(3), 701–6.

Haddad et al., J. Polym. Sci., Polym. Chem. Ed. (1974), 12(6), 1301–11.

Breslow et al., J. Appl. Polym. Sci. (1986), 32(4), 4657–61.

Barton et al., Comprehensive Organic Chemistry; "The Synthesis and Reactions of Organic Compounds", Vol. 2, pp. 562–568.

Torssell, Nitrile Oxides, Nitrones, and Nitronates in Organic Synthesis, "Novel Strategies in Synthesis", Table of Contents, 1988.

Kirk–Othmer, Encyclopedia of Chemical Technology, "Isocyanates, Organic", vol. 14, pp. 902–934.

Carey et al., Advanced Organic Chemistry, "Part B. Reactions and Synthesis", Third Edition, pp. 20–27, 1990.

Boyd et al., "The Reactions of Aliphatic Nitro Compounds: Condensations with isocyanates", JACS, vol. 75, Jun. 5, 1953, pp. 2762–2763.

Mukaiyama et al., "The Reactions of Primary Nitroparaffins with Isocyanates", JACS, Oct. 20, 1960, vol. 82, pp. 5339–534.

Bordwell et al., "The Taft Equation As Applied to Equilibrium Acidities of Nitroalkanes, $G(CH_2)_nNO_2$", J. Org. Chem. vol. 43, No. 16, 1978, pp. 3101–3107.

M. T. Shipchandler, "The Utility of Nitroacetic Acid and its Esters in Organic Synthesis", International Minerals & Chemical Corporation, Sep. 1979, pp. 666–686.

Whitney et al., Furoxans as Nitrile Oxide Percursors: Cycloaddition Reactions of Bis(Benzenesulfonyl) Furoxan, Tetrahedron Letters, vol. 22, No. 35, pp. 3371–3374, 1981.

Shimizu et al., The Reaction of Primary Nitro Compounds with Dipolarophiles in the Presence of ρ–Toluenesulfonic Acid, Bull. Chem, Soc. Jpn., 57.2531–2534 (1984).

Shimizu et al., "Reaction of 3,4–Disubstituted, 1,2,5–Oxadiazole 2–Oxides with Dipolarophiles", vol. 41, No. 4, pp. 727 to 738, 1985.

Shimizu et al., "A New Synthetic Method of alkyl Carbonocyanidate N–Oxides", Bull. Chem. Soc. Jpn., 58, 2519–2522 (1985).

Shimizu et al., Synthesis of Isoxazoline–3–carboxanilides and isoxazole–3–carboxanilides by Thermolysis of α–Methoxcarbonylα–nitroacetanilides in the Presence of dipolarophiles, Synthesis, Jun. 1986, pp. 488–490.

Shimizu et al., "A Convenient Preparative Method of Nitrile Oxides by the Dehydration of . . . ". Bull. Chem. Soc. Jpn., 59, 2827–2831 (1986).

Carey et al., Advanced Organic Chemistry, Third Edition, Part A: Structure and Mechanisms, 1990, pp. 20–27.

Wagener et al., "Thermally Reversible Polymer Linkages, 1. Model Studies of the Azlactone Ring", Macromolecules, vol. 24, No. 6, Mar. 18, 1991.

Wagener et al., "Thermally Reversible Polymer Linkages. 3. Covalently Cross–Linked Poly(azlactone)", Macromolecules, vol. 24, No. 26, Dec. 23, 1991.

Canary et al., "Thermally Reversible Crosslinking of Polystyrene via the Furan–Maleimide Diels–Alder Reaction", Journal of Polymer Science: Part A: Polymer Chemistry, vol. 30, 1755–1760 (1992), pp. 1755–1760.

March, "Aliphatic Nucleophilic substitution", Advanced Organic Chemistry, Reactions, Mechanisms, and Structure, Fourth Edition, pp. 365–473, Chapter 10, 1992.

Niyazymbetov et al., "Electrogeneration of the Anion of Ethyl Nitroacetate and Its Use in Electroorganic Synthesis", J. Org. Chem. 1993, 58, 779–783.

Diez–Barra et al., "Alkylation of Ethyl Nitroacetate in the Absence of Solvent", Synthetic Communications, 24(13), 1817–1821 (1994).

Leslie–Smith et al., "Divergent Behaviour in the Isocyanate–induced and Thermal Generation of Nitrile Oxides from Ethyl Nitroacetate", Tetrhedron Letters, vol. 35, No. 49, pp. 9251–9254, 1994.

Kuramoto et al., "Thermoreversible Reaciton of Diels–Alder Polymer Composed of Difurufuryladipate with Bismaleimidodiphenylmethane", Journal of Polymer Science: Part A: Polymer Chemistry, vol. 32, 2501–2504 (1994).

Ballini et al., "Amberlyst A–27, an Efficient heterogeneous Catalyst for the Michael Reaction of Nitroalkanes with β–Substituted Alkene Acceptors", J. Org. Chem. 1996, 61, 3209–3211.

Kurth et al., "Solid–Phase Combinatorial synthesis of Polyisoxazolines: A Two–Reaction Iteractive Protocol", J. Org. Chem. 1996, 61, 8755–8761.

Synthesis of Polyisoxazolines, J. Org. Chem., vol. 61, No. 25, 1996, pp. 8759–8761.

Corsaro et al., "The role of the Hydrogen Bonding in Cycloadditions of Benzonitrile Oxide with Cyanophenols", Tetrhedron, vol. 52, No. 23, pp. 7885–7892, 1996.

Maugein, "New Conditions for the Generation of Nitrile Oxides from Primary Nitroalkanes", Tetrahedron Letters, vol. 38, No. 9, pp. 1547–1550, 1997.

Prep'yalov et al.; Reaction of 2–substituted 6–alkoxy–4H–1, 3–oxazin–4–ones with some electrophilic and nucleophilic agents; Zh. Org. Khim. (1995), 31(8), 1237–40; St. Peterburg. Khim.–Farm.–Inst., Russia.*

* cited by examiner

*Primary Examiner*—Rabon Sergent
(74) *Attorney, Agent, or Firm*—Cynthia L. Foulke

(57) ABSTRACT

The present invention is directed to nitrile-oxide precursor compounds, and their preparation and use as an irreversible cross-linking agent in polymers having appropriate functionality, i.e., alkenes, alkynes nitriles, and isocyanates. The present invention is also directed to the use of nitrile oxide compound in filled or unfilled applications such as pressure sensitive adhesives, reactive hot melts, polyurethane dispersions, thermosetting adhesives, thermoplastic adhesives or coatings.

1 Claim, 13 Drawing Sheets

REAGENTS FOR HEAT ACTIVATED POLYMER CROSSLINKING

FIELD OF THE INVENTION

The present invention is directed to novel nitrile oxide precursor compositions and their preparation and use as polymeric crosslinkers.

BACKGROUND OF THE INVENTION

Reactive hot melt adhesives are typically thermosetting urethanes derived from polyols and diisocyanates which cure in the presence of moisture. Residual isocyanate in the urethane polymer mixture provides for crosslinking which takes place through moisture cure. Specifically, moisture cure affords extensions through urea formation, and crosslinking through biuret formation:

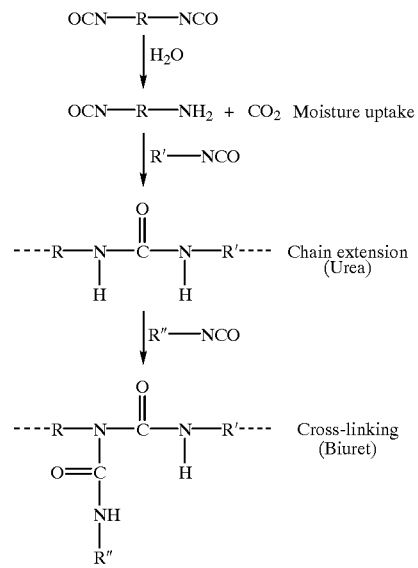

Depending upon the amount of humidity, this cure normally takes approximately 72 hours. It would be desirable to have a system which cures rapidly and is more controlled in that it does not dependent on available moisture. It would also be desirable to have a system which is applicable to "just-in-time" or "JIT" manufacture. That is, when the adhesive is applied to assemble a part, immediate cure to form a stable bond should be obtained so that the part can be shipped without delay. The adhesive should also have a pot stability for several hours at temperature typical for hot melt type adhesives, around 120° C. The present invention has found that such a system arises from using nitrile oxide precursor compounds which, when heated, form a thermally stable crosslink.

Nitrile oxides can be generated in situ by the reaction of hydroxamoyl chloride with a tertiary amine or other base. However this method can be corrosive because the Cl⁻ ion in the environment will attack metal surfaces. In addition, this method of generating nitrile oxide occurs at room temperature and therefore cannot be used in a one part hot melt system.

U.S. Pat. No. 3,931,106 discloses the in situ thermal decomposition of furoxans to produce dinitrile oxides which can then be used to modify a polyfunctional species, such as in polymer crosslinking. The dinitrile oxides produced by this method cure very rapidly at temperatures in the range of 80 to 110° C.

Nitrile oxides have also been generated from precursor compounds which are produced by a method involving the generation of the potassium enolate of ethyl nitroacetate in situ using $K_2CO_3$. The carbanion reacts with the electrophile, here phenyl isocyanate in toluene. Leslie-Smith, M. G., et al., Tet. Let. 1994, 35, 9251–9254. This method however provides low yields, 30% of an aromatic precursor compound.

Therefore a need exists for aliphatic nitrile oxide precursor compounds and for faster curing of reactive hot melts which are non-moisture curing. A need also exists for a more controlled crosslinking system than is currently possible with the isocyanate moisture cure chemistry.

SUMMARY OF THE INVENTION

The present invention is directed to difunctional nitrile-oxide precursor compounds, and their preparation and use as an irreversible crosslinking agent in polymers having appropriate functionality, i.e., alkenes, alkynes, nitriles and isocyanates. The present invention is also directed to the use of nitrile oxide compounds in filled and unfilled applications such as reactive hot melts, pressure sensitive adhesives, polyurethane dispersions, thermosetting adhesives, thermoplastic adhesives, and coatings.

Specifically, the present invention is directed to the preparation of novel nitrile oxide precursor compounds via the generation of the potassium enolate of ethyl nitroacetate followed by isolation of the enolate prior to the addition of an electrophile (i.e., a diisocyanate) in a polar solvent such as monoglyme or diglyme.

The present invention is further directed to novel nitrile oxide precursor compounds of the general formula:

Formula I

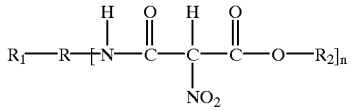

wherein R is a substituted or unsubstituted $C_{1-17}$ alkyl, alkoxy, cycloalkyl, aromatic or diisocyanate trimer; n is 1–10; $R_1$ is selected from the group consisting of NCO, CN, H, $SO_2Cl$, COCl, $N(CH_3)_2$ $C(O)CH_3$, $C(O)OCH_3$, $C(O)OC_2H_5$, $C_6H_5$, an acid chloride such as $SOCl_2$, or another group with reactive functionality such as vinyl, or

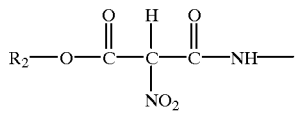

wherein $R_2$ is branched or unbranched alkyl with 1 to 5 carbon atoms such as ethyl, isopropyl or sec-butyl, and the like; provided that Formula I cannot be derived from p-phenylene diisocyanate ("PPDI").

DESCRIPTION OF THE FIGURES

The above and other features of the invention will be further described in the following detailed specification considered in conjugation with the accompanying drawings in which.

DETAILED DESCRIPTION OF THE INVENTION

Figure 1:
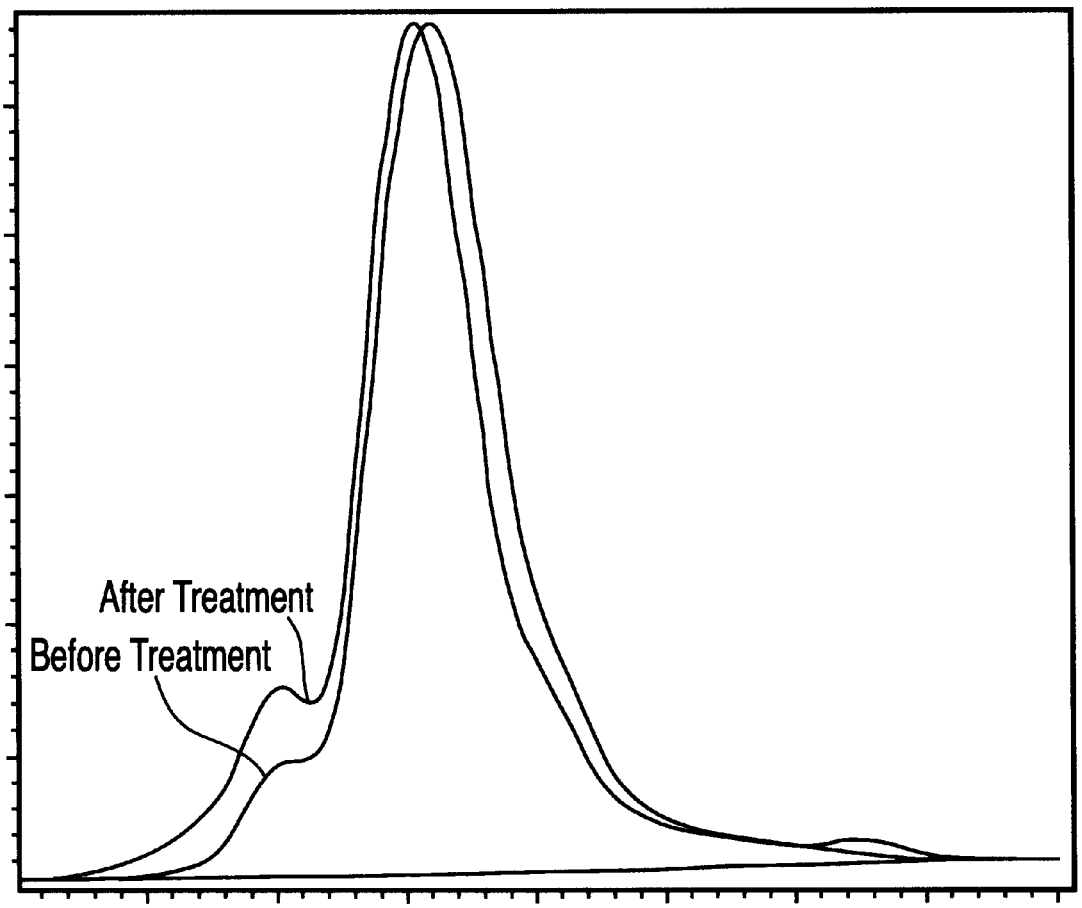
FIG. 1 is a gel permeation chromatograph ("GPC") showing increased molecular weight of RICON 130.

The present invention is directed towards novel nitrile oxide precursor compounds, the process of making these compounds, and the use of these compounds in the crosslinking of functional polymers by reaction of the nitrile oxide formed upon heating with a functional group on the polymer.

The nitrile oxide precursor compounds of the present invention are of the general formula:

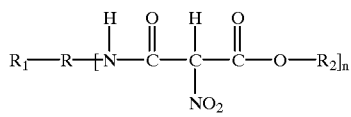

Formula I wherein R is a substituted or unsubstituted $C_{1-17}$ alkyl, alkoxy, cycloalkyl, aromatic or diisocyanate trimer; n is 1–10; $R_1$ is selected from the group consisting of NCO, CN, H, $SO_2Cl$, COCl, $N(CH_3)_2$, $C(O)CH_3$, $C(O)OCH_3$, $C(O)OC_2H_5$, $C_6H_5$, an acid chloride such as $SOCl_2$, or another group with reactive functionality, or

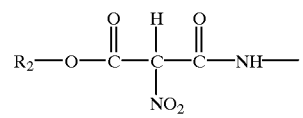

wherein $R_2$ is branched or unbranched alkyl with 1 to 5 carbon atoms such as ethyl, isopropyl or sec-butyl, and the like; provided that Formula I cannot be derived from p-phenylene diisocyanate ("PPDI").

R may be branched or unbranched, substituted or unsubstituted with alkyl, sulfate, sulfonate, alkoxy, CN, $NO_2$ or an aromatic group. R may be a biphenyl group, fused rings or repeating aromatic groups.

R is derived from an aromatic or aliphatic residue of an isocyanate, diisocyanate, or polyisocyanate compound. Examples of R include residues of the following isocyanate, diisocyanate, or polyisocyanate compounds:

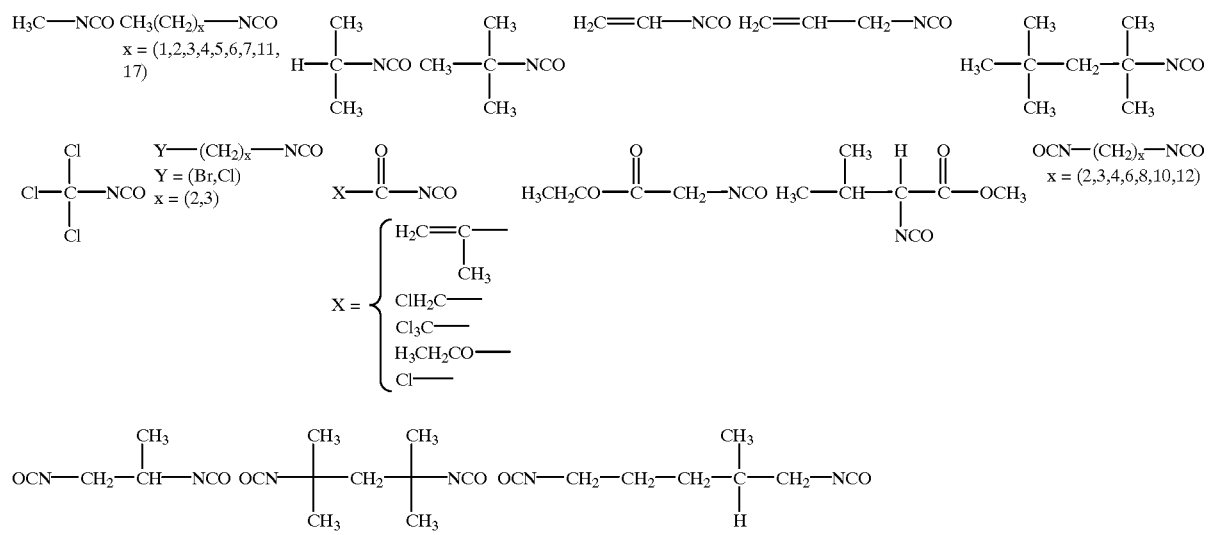

-continued
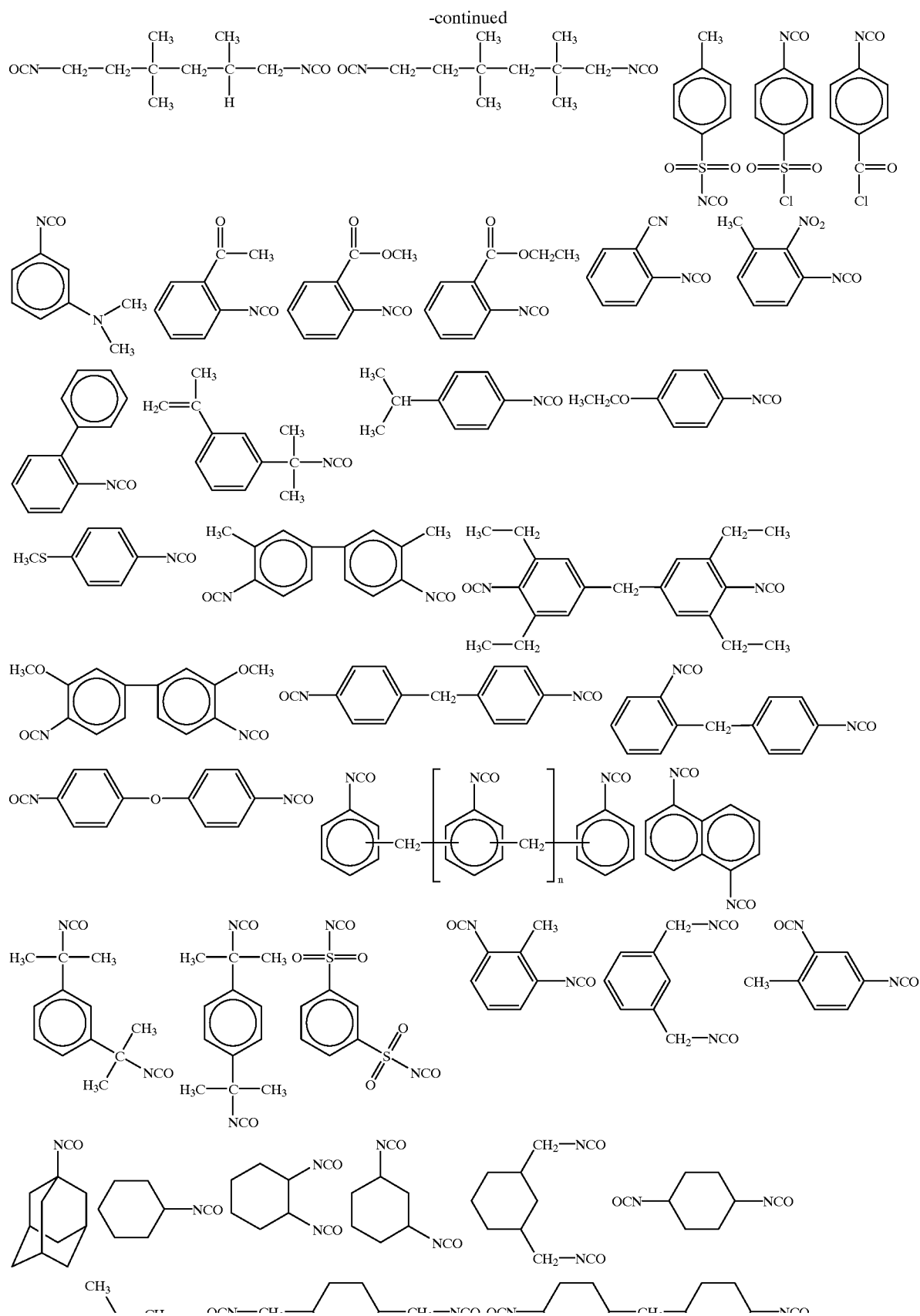

wherein in the above structures, n=2–4, and x and y are chosen so that the molecular weight of the polyneopentyl glycol adipate diisophorone terminated isocyante structure is approximately 1350.

Aromatic nitrile oxide precursor compounds of the present invention can undergo a reversion process under certain conditions to reform an isocyanate. An example of this reversion occurs with the nitrile oxide precursor derived from phenyl isocyanate in the presence of the solvent triglyme:

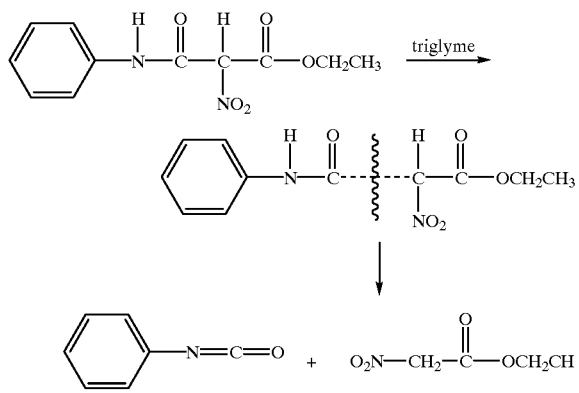

In fact, unexpectedly, nitrile oxide precursors, derived from aromatic isocyanates wherein the NCO is in direct conjugation with the aromatic ring will preferentially undergo the reversion back to isocyanate in the presence of ethers, esters, polyethers or polyesters. Polyesters and polyethers are typical components of hot melt systems. If reversion to the isocyanate occurs, there is no pathway to nitrile oxide and crosslinking or chain extension is prevented.

For crosslinking or chain extension to occur effectively, the reversion process must be eliminated or minimized.

Therefore, a blend of polyether or polyester based hot melt with an aromatic nitrile oxide precursor should be avoided to provide maximum crosslinking. Such aromatic based nitrile oxide precursors can be used in hot melt systems based on other polymers such as polybutadiene or polyisoprene which do not comprise polyethers or polyesters.

Therefore, in one embodiment of the present invention, the nitrile oxide precursor is derived from an isocyanate having an alkyl group between the aromatic ring and the isocyanate group preventing reversion by disrupting the conjugation. For example if the nitrile oxide precursor is derived from tetramethylene-xylenediisocyanate, ("TMXDI") reversion does not occur.

In another embodiment, the nitrile oxide precursor is derived from an aliphatic isocyanate which will not revert back to the isocyanate compound. In both embodiments, the hot melt polymer may optionally comprise polyethers or polyesters, or these can be absent as in the case of polyisoprene.

The properties of the nitrile oxide precursor compounds of the present invention will differ depending on the nature of the functionality (variable R in Formula I) between the active sites, i.e., nitrile oxide precursor functionality, on the compound. For instance, some precursors may provide better solubility in one certain polymer system than another. Also, difunctional precursors may have different reactivity depending on whether the active site is located at a primary, secondary or tertiary position. For example, the precursor derived from isophorone diisocyanate actually has active sites located at both primary and secondary positions. An example of a nitrile oxide precursor with active sites in a tertiary position is the one derived from TMXDI.

Examples of new nitrile oxide precursors within the scope of the present invention are shown below:

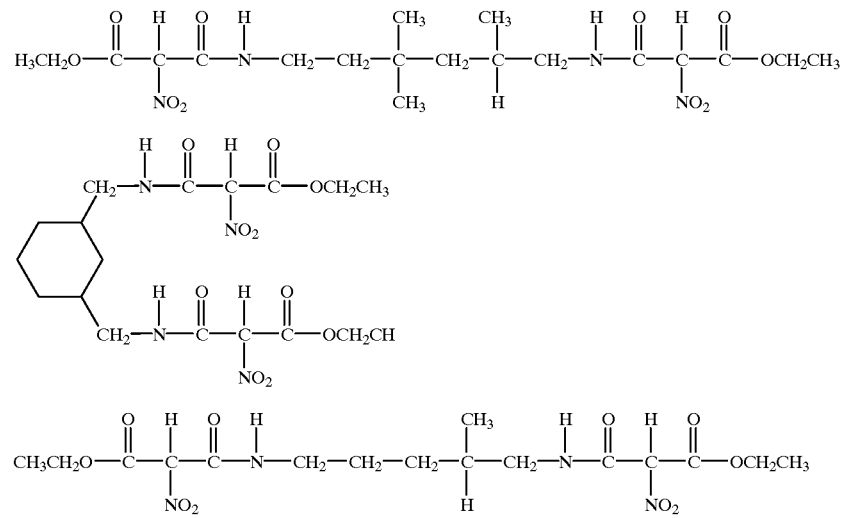

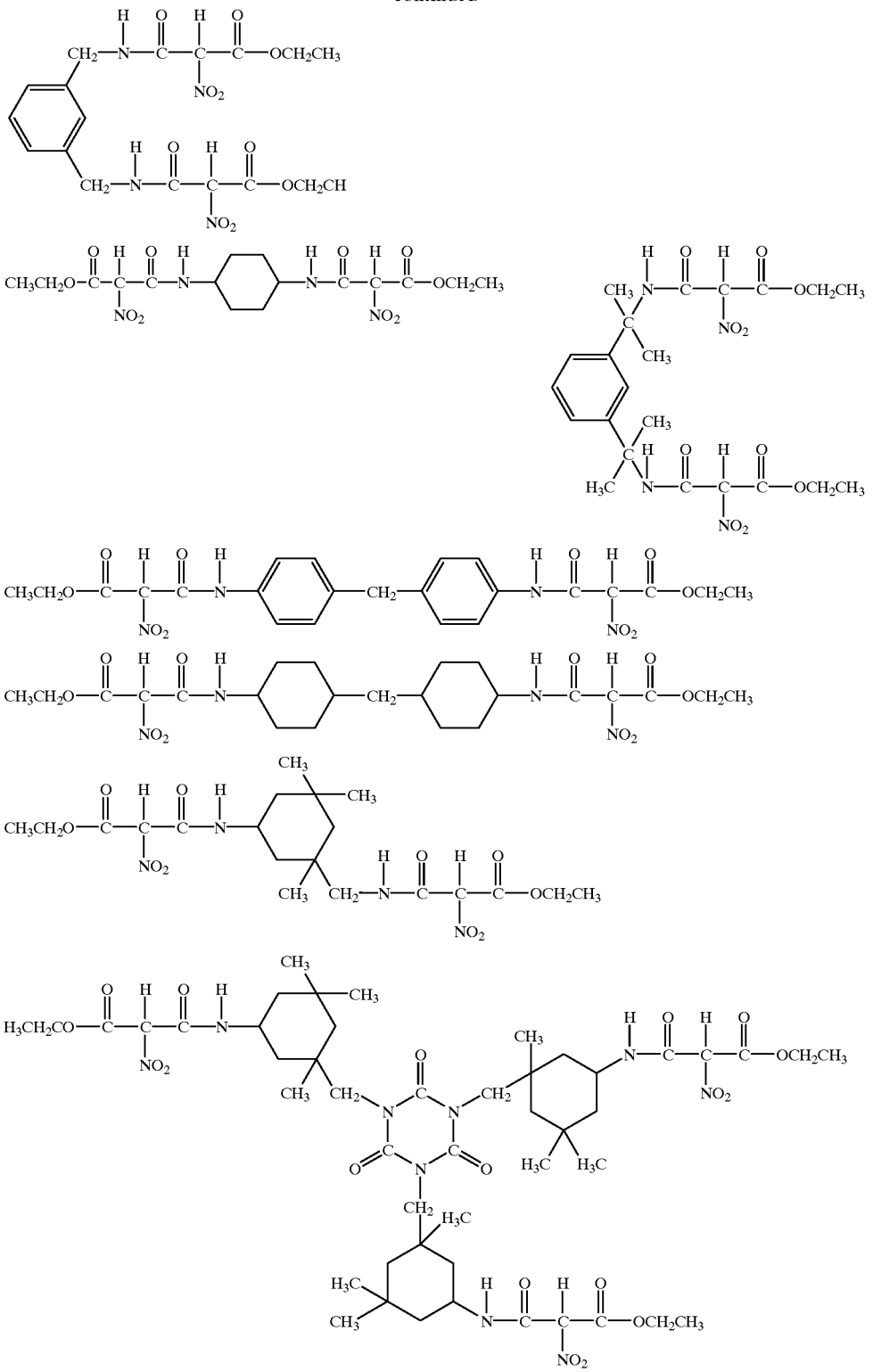

There are two criteria that a suitable nitrile oxide precursor must meet: 1) a melt temperature in the polymeric adhesive system that is less than or equal to the decomposition temperature of the precursor; and, 2) solubility in the polymer system to be crosslinked upon melting. Therefore the choice of the most appropriate nitrile oxide precursor will depend on compatibility in the unreacted polymer blend and the level of crosslink density required to develop the properties required for a particular application.

The difunctional nitrile-oxide precursors of the present invention serve as an irreversible chain extension or crosslinking agent in polymers having appropriate functionality to react with the nitrile oxide, e.g., alkene, alkyne, nitrile or isocyanate. Mixtures of a polymer bearing reactive sites or unsaturated functionality and a precursor compound of the present invention having two reactive sites (difunctional) will have a pot stability at about 120° C. such that there is less than 20% viscosity advancement per hour. These materials generate a very rapid cross-link or chain extend at elevated temperatures (>150° C.).

At the decomposition temperature of the nitrite oxide precursor compound, $CO_2$ and alcohol are evolved from the sample generating the nitrile oxide species:

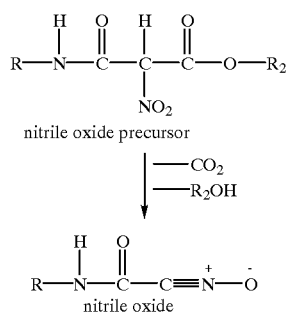
nitrile oxide precursor $$\downarrow \begin{array}{l} -CO_2 \\ -R_2OH \end{array}$$

nitrile oxide

Since nitrile oxides are known to be a very reactive and unstable species, once the nitrile oxide is formed it reacts very rapidly with an unsaturated functionality on the polymer (e.g., alkene, alkyne, nitrile, or isocyanate).

An example of such a crosslinking reaction is the reaction of the nitrile oxide compound with an olefin, via a 1,3-dipolar addition, to yield an isoxazoline structure, also referred to as an isoxazoline adduct:

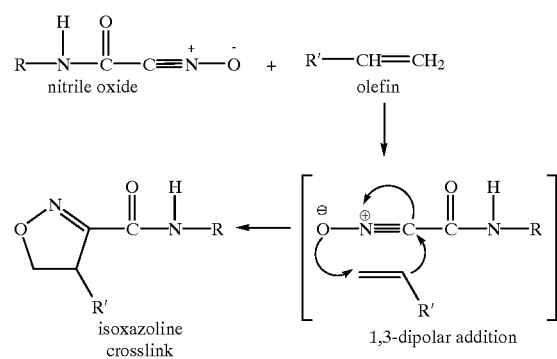

In the above general schematic, R' represents a polymer chain.

A specific example with an alkene, e.g., 1-dodecene, is shown below with the isoxazoline adduct which serves as the crosslink:

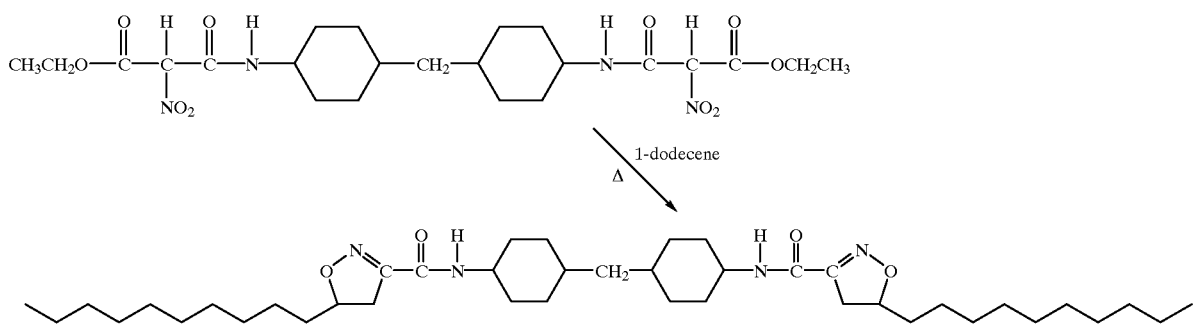

In the case of a reactive hot melt adhesive formulation that contains unsaturation (olefin) in addition to residual isocyanate, designated in the schematic below as "RHM", a dual curing mechanism is possible. Reactive hot melts are one-component, 100% solid, solvent-free urethane prepolymers. Unlike conventional hot melt adhesives that can be repeatedly heated from its solid state and flowed to a liquid form, the reactive hot melts behave as a thermoset and undergo an irreversible chemical reaction once dispensed in the presence of ambient moisture. In the dual curing system described herein, crosslinking will be rapidly supplied by nitrile oxide reacting with the unsaturation (olefin) incorporated into the reactive hot melt. Further crosslinking will then later be supplied through moisture cure on the residual isocyanate present on the reactive hot melt. Hence, nitrile oxide crosslinking provides the initial strength while moisture cure provides the additional strength to result in a fully cured system. This dual cure system is represented schematically below:

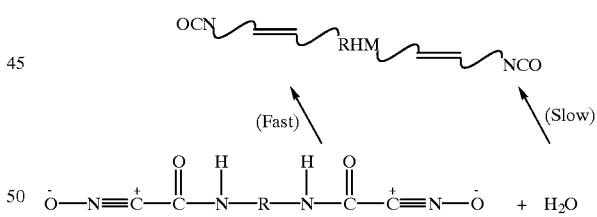

It is desirable for the crosslinking reactions to occur very rapidly at elevated temperatures such as 180° C., and in fact they do occur very rapidly at 180° C. However, at temperatures of 120° C. and 100° C. it is desired that no or very little reaction take place since this represents the pot temperature at which a typical hot melt adhesive formulation is kept in the application equipment. No reaction is observed at 60° C. At 120° C. and 100° C., formation of the isoxazoline adduct occurs but at a slower rate. Preferably the mixture of the polymer and difunctional nitrile oxide precursor compound should have a pot stability at about 120° C. such that there is less than 20% viscosity advancement per hour, however it should generate a very rapid crosslink at elevated temperatures greater than 150° C. This is in contrast to U.S. Pat. No. 3,391,106 which discloses the in situ thermal decomposition of furoxans to produce dinitrile oxides which can then be used to modify a polyfunctional species, such as in polymer crosslinking. The dinitrile oxides produced by this method cure very rapidly at temperatures in the range of 80 to 110° C.

The isocyanate functionality, from which the precursor is made, may be present on a polymer backbone or terminal position. In one embodiment, the polymer is prepared by polymerizing, or co-polymerizing, an isocyanate compound having a pendant polymerizable functional group such as a vinyl group, e.g., 1-(1-isocyanato-1-methyl ethyl)-3-(1-methyl ethenyl)benzene ("m-TMI"), followed by formation of the nitrite oxide precursor compound. This method is preferred over the method where the nitrite oxide precursor is formed first and then polymerized through an available vinyl group.

Another embodiment, represented below by the reaction of m-TMI with a vinyl derivative produces an AB copolymer which can then be made into the nitrile oxide precursor.

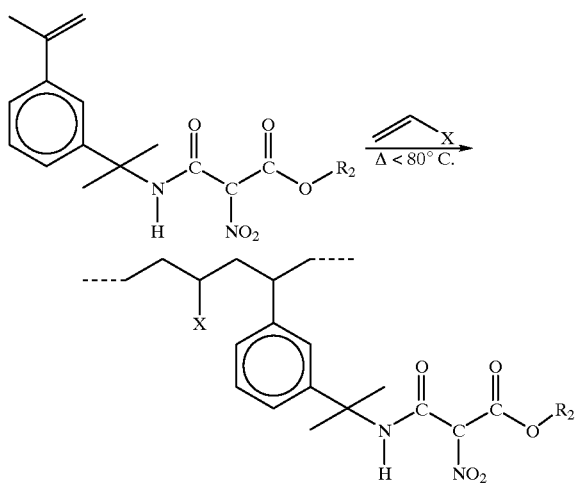

The precursor compounds of the present invention are prepared by a novel process involving the steps of generating a potassium enolate of alkyl nitroacetate; isolating the enolate; then adding to the enolate an electrophile such as a diisocyanate in a polar aprotic solvent such as monoglyme. The salt of the precursor is then protonated to the neutral precursor compound.

The prior art method involves the generation of the potassium enolate of ethyl nitroacetate ($K^+ENA^-$) in-situ, using $K_2CO_3$ followed by reacting the carbanion with an electrophile. Leslie-Smith, M. G., et al., Tet. Let. 1994, 35, 9251–9254. It has been found, in accordance with the present invention, that if the $K^+ENA^-$ salt is isolated under inert conditions using a different base, ethanolic KOH, prior to the introduction of the electrophile, higher yields are obtained than by the prior art method. The use of KOH as base eliminates the potential generation of water that is possible using potassium carbonate.

The precursor compounds of the present invention are prepared in the presence of a polar aprotic solvent, specifically solvents having high dielectric constants but lacking hydroxyl groups or other hydrogen-bonding functionalities. Examples of such solvents are tetrahydrofuran (THF), dimethylformamide (DMF), dimethyl sulfoxide (DMSO), 1,2-dimethoxyethane (monoglyme) and 2-methoxyethylether (diglyme). The preferred solvent to use for preparing the precursor compounds of the present invention is diglyme or monoglyme. It has surprisingly been found that diglyme and monoglyme, both polar solvents, can be effective for C-alkylation. This is unexpected, because more polar solvents tend to favor O-alkylation while, less polar solvents favor C-alkylation. O-alkylation of the enolate is not desired. It has been found, in accordance with the present invention, that not only did polar solvents like diglyme favor C-alkylation, but the solvent also allowed the diisocyanates to stay in solution longer affording difunctionalized products. Diglyme is the most preferred solvent because it has a higher boiling point and therefore higher reaction temperatures can be used.

Monoglyme requires three to four days at 70 to 80° for the reaction to be complete, while the reaction with diglyme is complete in less than 16 hours at 100° C.

The prior art discloses the generation of nitrile oxide precursor compounds from aromatic isocyanate precursors using toluene as the solvent and enolate generated in situ using potassium carbonate as base. The prior art reaction takes 3 to 5 days to complete. In addition, the prior art reaction conditions are ineffective at transforming aliphatic isocyanates into nitrile oxide precursors. Leslie-Smith, M. G., et al., Tet. Let. 1994, 35, 9251–9254. As described in the present invention, using monoglyme as the solvent in place of toluene, when reacting the potassium enolate with the electrophile, provides a significant advantage in the production of aliphatic based and difunctional nitrile oxide precursors. The use of monoglyme and the preformed potassium enolate resulted in (1) increased yields of nitrile oxide precursors, (2) generation of difunctional nitrile oxide precursors, and (3) the preparation of aliphatic nitrile oxide precursors.

When making the nitrile oxide precursor, the product resulting from the potassium enolate and isocyanate reaction is typically in the K+ salt form as a solid suspension in monoglyme. Hence it is necessary to isolate the salt, disperse in THF, add acidic ion exchange resin, and heat to 40 to 50° C. in order to protonate the nitrile oxide precursor.

The nitrile oxide precursors of the present invention are useful in both filled and unfilled applications such as pressure sensitive adhesives, reactive hot melts and polyurethane dispersions. Examples of uses for reactive hot melts are in panels, such as in office partitions, garage and entry doors, the exterior side walls of recreation vehicles, and in automobiles, both interior: panels, carpet, and exterior: head and tail light.

The following examples are merely illustrative and not intended to limit the scope of the present invention in any way.

EXAMPLE 1

Generation and isolation of preformed enolates of ethyl nitroacetate, alkylation with electrophile, and work up of protonated nitrile oxide precursor is discussed below:

A 3L 3-necked round bottom flask and slow addition funnel were oven dried (180° C.) before applying grease and septa. The glassware was then pumped and purged with nitrogen to evacuate the system and supply a blanket of nitrogen. Ethyl nitroacetate (0.330 mol) was introduced through the septa into the slow addition funnel. Ethanol (30 mL) was added via syringe to rinse down sides of the slow addition funnel. The flask containing ethyl nitroacetate and ethanol was chilled to −78° C. using a dry ice/acetone bath. A solution of potassium hydroxide (0.315 mol) in ethanol was added by cannula into the slow addition funnel which was subsequently delivered into the reaction vessel. Ethanol (50 mL) was added via syringe to rinse down sides of the slow addition funnel and the dry ice/acetone bath was then removed to allow the reaction to reach room temperature. The flask was then connected to a trap, immersed in a warm water bath, and subjected to vacuum to remove ethanol and retain solid enolate.

Dry monoglyme(1,2-dimethoxyethane,ethylene glycol dimethyl ether) or diglyme (2-methoxy ethyl ether) (60 mL) was added by cannula under nitrogen. To this solution was added the difunctional electrophile (0.1575 mol, 41.3 g DESMODUR W, a diisocyanate available from Bayer), which was dissolved in monoglyme or diglyme (200 mL) and delivered by air-sensitive syringe techniques. Reactions were initiated at room temperature and later on adjusted to 85 to 100° C. depending on which solvent was used:

| Solvent | Temp. | Rxn. Time (hrs.) |
|---|---|---|
| monoglyme | 85° C. | ~72 |
| diglyme | 100° C. | <16 |

The progress of the reaction was determined through infrared analysis by observing the disappearance of isocyanate at 2260 cm$^{-1}$. Reactions that used acid chlorides or sulfonyl chlorides in place of isocyanates as electrophiles, did not require protonation in the work-up to yield the final product since potassium chloride is eliminated, see Scheme 1. Once all isocyanate was consumed, the salt form of the precursor was isolated by vacuum filtration using a Buchner funnel. The salt was washed with THF and then air dried. In the salt form, the two carbonyls due to the ester and amide were located at 1690, and 1630 cm$^{-1}$, respectively and the C—O single bond stretch was found at 1070 cm$^{-1}$.

The salt form of the nitrite oxide precursor was then added to a 4L 3-necked flask and then dispersed in tetrahydrofuran (THF) using an overhead mechanical stirrer. To this flask was added strongly acidic amberlyst ion exchange resin and the reaction mixture was heated overnight at 40° C. using a water bath. Once the salt form of the precursor was protonated it became soluble in THF and was isolated from the ion exchange resin by vacuum filtration using a Buchner funnel. THF was then removed from the nitrite oxide precursor by stripping under vacuum using a rotary evaporator. Toluene was then added to the oil and swirled to dissolve any residual ethyl nitroacetate and then this was decanted from the oil. This was repeated several times to make sure all residual ethyl nitroacetate was removed. Tetrahydrofuran was added, mixed in to dissolve the material, and removed under vacuum which subsequently also removed any residual toluene and resulted in a solid material. The clean nitrile oxide precursor derived from DESMODUR W remained. The structures were confirmed by IR, and NMR analysis. IR NH 3300 cm$^{-1}$, ester C=O 1760 cm$^{-1}$, amide C=O 1680 cm$^{-1}$, C—O 1020 cm$^{-1}$.

H-NMR NH 8.5 ppm, CH 6.5, 5.5 ppm, CH$_2$ 4.5 ppm, CH$_3$ 1–2 ppm.

Using this general procedure, the following novel nitrile oxide precursors were isolated and characterized, see Table 1.

TABLE 1

Nitrile Oxide Precursors

| Structure | $^1$H-nmr (PPM) NH, CH, CH$_2$, CH$_3$ |
|---|---|
| A (structure with CH$_3$CH$_2$O—C(=O)—C(NO$_2$)H—C(=O)—NH— linked to trimethylcyclohexane with CH$_2$—NH—C(=O)—C(NO$_2$)H—C(=O)—OCH$_2$CH$_3$) | 8.6, 6.3, 4.3, 1.3 |
| B (structure with CH$_3$CH$_2$O—C(=O)—C(NO$_2$)H—C(=O)—NH—cyclohexyl—CH$_2$—cyclohexyl—NH—C(=O)—C(NO$_2$)H—C(=O)—OCH$_2$CH$_3$) | 8.5, 6.3, 4.2, 1.3 |
| C (cyclohexane with two CH$_2$—NH—C(=O)—C(NO$_2$)H—C(=O)—OCH$_2$CH$_3$ arms) | 8.6, 6.3, 4.2, 1.3 |

TABLE 1-continued

Nitrile Oxide Precursors

| Structure | $^1$H-nmr (PPM) NH, CH, CH$_2$, CH$_3$ |
|---|---|
| D (structure) | 9.2, 6.4, 4.3, 1.2 |
| E (structure) | 8.9, 6.3, 4.2, 1.2 |
| F (structure) | 8.6, 6.3, 4.2, 1.2 |
| G (structure) | 8.6, 6.2, 4.2, 1.2 |
| H (structure) | 8.5, 6.2, 4.2, 1.3 |
| I Precursor derived from Rubinate 1790 | 10.7, 6.5, 4.2, 1.2 |
| J (structure) | 10.7, 6.5, 4.2, 1.2 |
| K (structure) | 9.3, 6.2, 4.2, 1.3 |

EXAMPLE 2

Crosslinking Studies on RICON 130

This example shows the crosslinking of difunctional nitrile oxide precursors with unsaturated polymer systems. The polymer used was RICON 130 which is a 2500 Mn polybutadiene with 30 mole percent vinyl functionality. The difunctional aliphatic precursor used was that derived from IPDI prepared according to Example 1 (Structure A in Table 1) and the mole ratio of precursor to vinyl unsaturation was (1:80). The mole ratio of precursor to all available olefin was (1:264). This example was conducted by mixing the precursor, RICON 130, and dichlorobenzene in a small jar containing a stir bar. This jar was then immersed into a 120° C. oil bath for ~5 hours while stirring and then a sample was removed and analyzed by GPC. Although the level of precursor used was small, a noticeable increase in molecular weight can be seen in the GPC overlay shown in FIG. 1. By comparing the areas, one can see that an increase from 6 to 14% relative area is found for the higher molecular weight component at 18 minutes.

EXAMPLE 3

Crosslinking Studies on ISOLENE 400

This example shows the crosslinking of ISOLENE 400 which is a 90,000 MW polyisoprene containing 92 mole percent unsaturation with a difunctional nitrile oxide precursor derived from DESMODUR W which was prepared according to Example 1 (Structure B in Table 1) and then dispersed in ISOLENE 400 at a temperature of 70° C. The crosslinking study was conducted by mixing the reagents in a small jar containing a stir bar which was then immersed into a 120° C. oil bath for ~6 hours. Dichlorobenzene was used as a diluent. Samples were withdrawn periodically for analysis by gel permeation chromatography (GPC). The mole ratio of precursor to unsaturation was (1:237) in order to eliminate any chance of gelation which would hinder analysis by GPC. The amount of precursor to unsaturation was small; however, after six hours of reaction, a noticeable increase in molecular weight could be seen in the GPC curve due to crosslinking.

Figure 2:
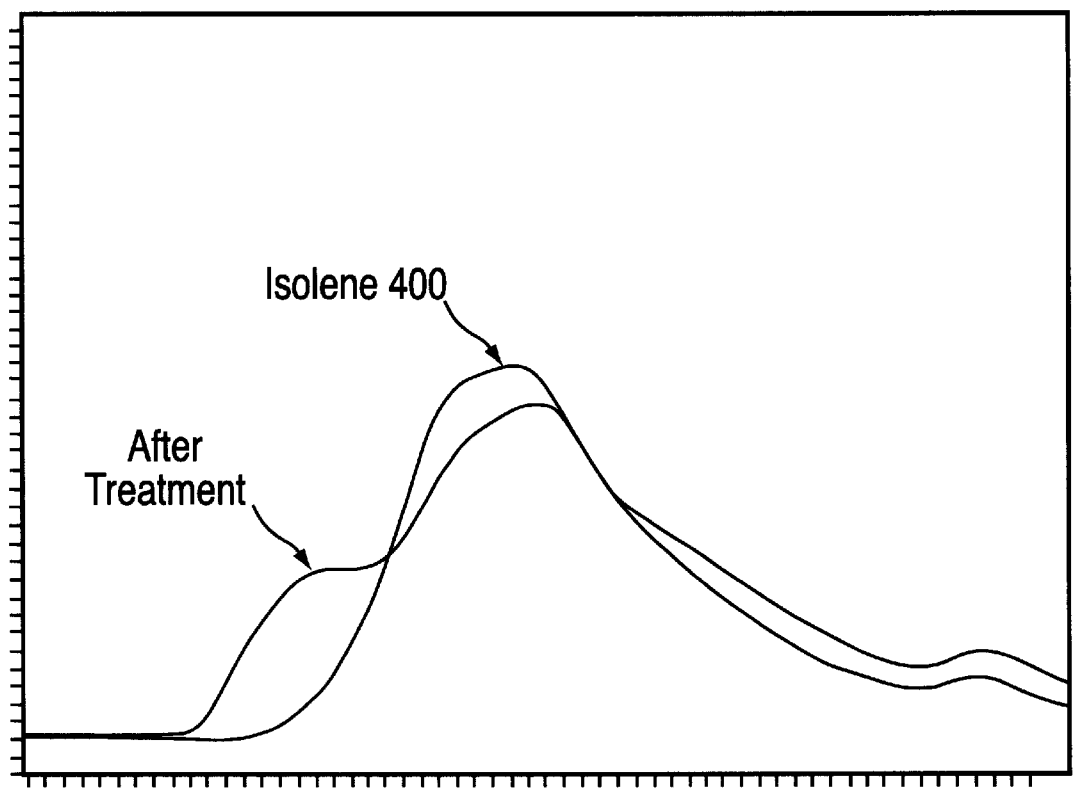
FIG. 2 is a GPC overlay of increased molecular weight polymer and ISOLENE 400, where the nitrile oxide precursor to olefin ratio is 1:100.

Since no gelation occurred using the ratio of (1:237), another experiment was conducted using a higher level of nitrile oxide precursor (e.g., 1:100). When this experiment was carried out, samples were removed periodically for GPC analysis. We found that crosslinking took place after 3.5 hours resulting in gelation. In addition, a sample removed ~10 minutes prior to gelation showed a substantial increase in molecular weight as shown in the GPC in FIG. 2.

In addition to the two experiments above, a third experiment was conducted using a ratio of (1:20) which resulted in crosslinking (gelation) occurring in less than one hour.

EXAMPLE 4

Crosslinking of Allyl Alcohol Capped Reactive Hot Melt

A polyurethane reactive hot melt which contained two weight percent residual isocyanate was reacted with allyl alcohol to cap the isocyanate and provide a point of unsaturation for the nitrite oxide to react with once formed. This capped reactive hot melt was then used as the unsaturated substrate in the reaction with the difunctional aliphatic nitrite oxide precursor derived from IPDI (Structure A, Table 1). There was no need for any co-solvent since the difunctional aliphatic nitrite oxide precursor was soluble in the capped reactive hot melt. The mole ratio of precursor to unsaturation was 1:2. The amount of increase in molecular weight was not expected to be great in this experiment since only 2.0 weight percent allyl functionality on the reactive hot melt would be available to react. However, the molecular weight distribution of the GPC curve changed after reaction showing the formation of higher molecular weight material. The Mn was found to change from 9542 to 9686 and the Mw changed from 21,565 to 24,380.

This type of information will be necessary for determining the level of unsaturation required in the reactive hot melt to provide the necessary crosslinking level which should translate to the required adhesive performance.

EXAMPLE 5

Reactive Hot Melt Viscosity Studies

This experiment utilized rheometric dynamic analysis ("RDA") which measured the increase in viscosity which indicates an increase in green strength. Pot stability was tested using a 2.6% allyl capped reactive hot melt and the difunctional nitrile oxide precursor derived from DESMODUR W (Structure B, Table 1). The mole ratio of unsaturation to nitrile oxide precursor was (10:1) and the temperature investigated was 100° C. The results show a 2.5% viscosity increase per hour. This value is much better than the required amount of <20% viscosity per hour necessary for reactive hot melt applications.

The above was repeated using 150° C. instead of 100° C. For comparison, a control free of precursor was also evaluated. These results, shown in FIG. 3, indicate a considerable rise in viscosity (Eta*) when precursor is used, and no increase in viscosity when nitrile oxide is not present.

Figure 3:
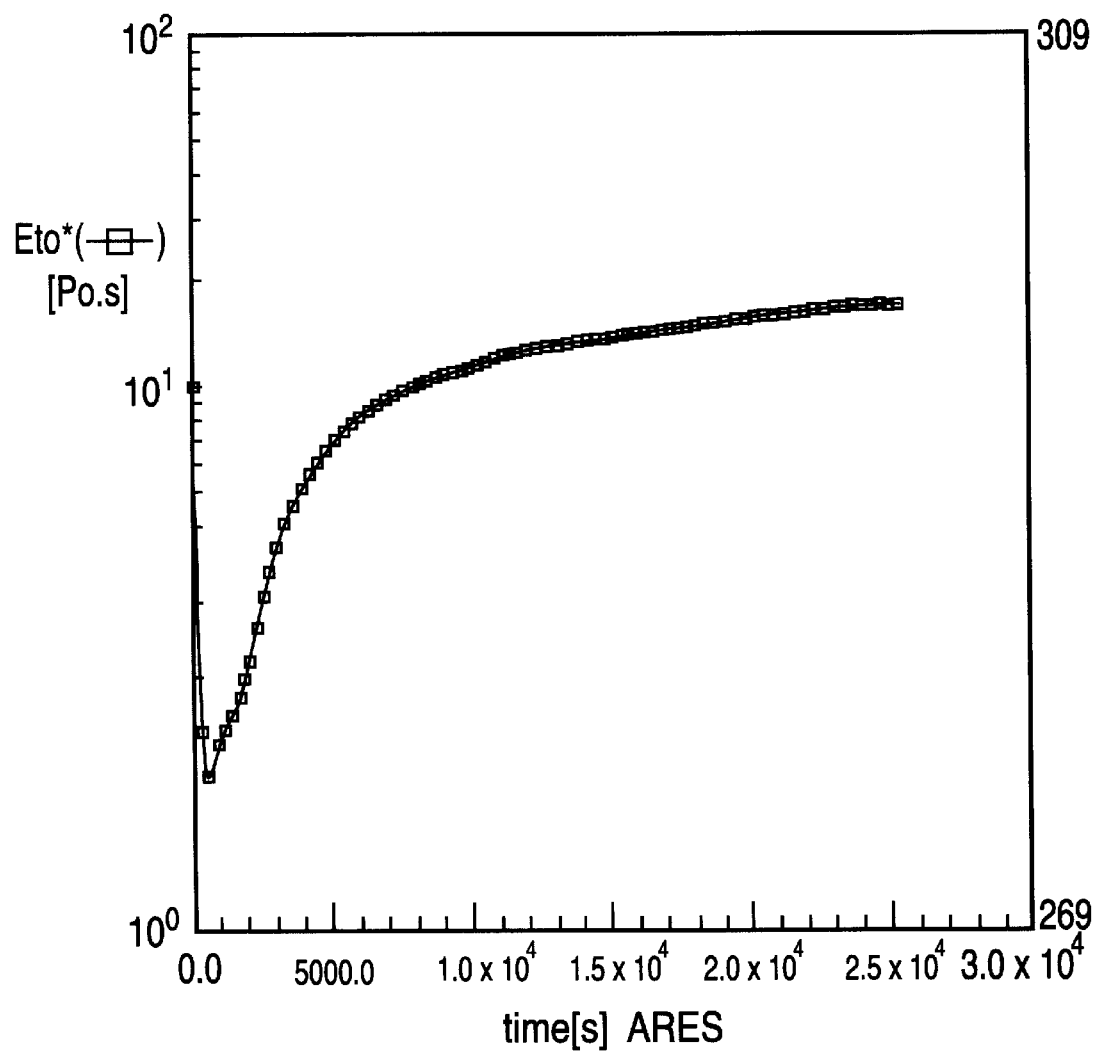
FIG. 3 is a rheometric dynamic anaylsis ("RDA") curve showing the viscosity increase, as a function of time, of a 2.5% allyl capped reactive hot melt adhesive formulated with difunctional nitrile oxide precursor at 150° C.

These results in FIG. 3 indicate that the increase in viscosity is due to nitrile oxide crosslinking. As seen in the figure, the viscosity initially decreases as the formulation heats 10° C./min to 150° C. Then the temperature is held constant at 150° C., as a result the viscosity then increases due to crosslinking with the nitrile oxide (i.e., chain extension), then levels off after two hours since all nitrile oxide has formed and crosslinked.

EXAMPLE 6

Initiation of Nitrile Oxide Precursor to Nitrile Oxide Using a Short Temperature Spike The rate at which the aliphatic nitrile oxide precursor derived from cyclohexyl isocyanate (Structure H, Table 1) decomposes to nitrile oxide and then subsequently reacts with 1-dodecene has been shown to be complete within five minutes when heated to 180° C.

This example was conducted to determine the minimum time/temperature protocol required to fully convert all nitrile oxide precursor to nitrile oxide and form adduct with 1-dodecene (unsaturated molecule). Since the rate determining step is conversion of nitrile oxide precursor to nitrile oxide, the rate can be determined by detection of adduct formation through HPLC. In order to investigate this issue three reactions were conducted. In all cases, the reaction mixture consisted of aliphatic monofunctional nitrile oxide precursor derived from cyclohexyl isocyanate and 1-dodecene in a (1:100) mole ratio contained in a small vial. These vials were then submersed into a 100° C. oil bath for 30 minutes to equilibrate at this temperature and to simulate hot melt pot temperature. It is also known that precursor reactivity at this temperature is relatively low. Each vial was then submersed into a 180° C. oil bath for one, two, or three minutes and then removed and allowed to cool to room temperature. The conditions were chosen to simulate an elevated temperature spike delivered to the adhesive system immediately prior to application, such as might be the case for a heated spray nozzle. While at room temperature, samples were removed after several minutes for HPLC analysis.

The results, in Table II below, show that a very high percent of the precursor was converted to isoxazoline adduct with a one minute 180° C. temperature spike. After the vial was removed from the 180° C. oil bath and cooled to room temperature ~88% of the precursor was converted to adduct. The results also show that a 180° C. temperature spike for three minutes and followed by cooling to room temperature for five minutes was sufficient to convert all precursor to the adduct.

Therefore, it appears that the transformation from nitrile oxide precursor to isoxazoline adduct is sufficiently rapid at 180° C. to provide crosslinked polymer with only a short high temperature exposure to minimize degradation of the polymeric adhesive or the substrate. Shown in the table below are the conditions used in conducting the experiments and the amount of adduct formed in relation to the amount of unconsumed precursor.

TABLE II

| Conditions | % Conversion of precursor to adduct |
| --- | --- |
| 180° C. 1 min., r.t. 5 min. | 76.6 |
| 180° C. 1 min., r.t. 30 min. | 78.2 |
| 180° C. 1 min., r.t. 3 hrs. | 86.1 |
| 180° C. 1 min., r.t. final. | 88.3 |
| 180° C. 2 min., r.t. 5 min. | 81.0 |
| 180° C. 2 min., r.t. 10 min. | 83.0 |
| 180° C. 2 min., r.t. 30 min. | 84.8 |
| 180° C. 2 min., r.t. 1 hr. | 86.5 |
| 180° C. 3 min., r.t. 2 min. | 90.7 |
| 180° C. 3 min., r.t. 5 min. | 99.5 |

EXAMPLE 7

The same procedure followed in Example 6 was repeated at different temperatures. The time required for 100% conversion at each temperature are shown below in Table III.

TABLE III

| Temperature | Time | % Conversion |
| --- | --- | --- |
| 120° C. | 5 hours | 100 |
| 100° C. | 24 hours | 100 |
| 80° C. | 110 hours | 100 |
| 60° C.* | 144 hours | 0 |

*precursor is stable at this temperature and below

Figure 8:
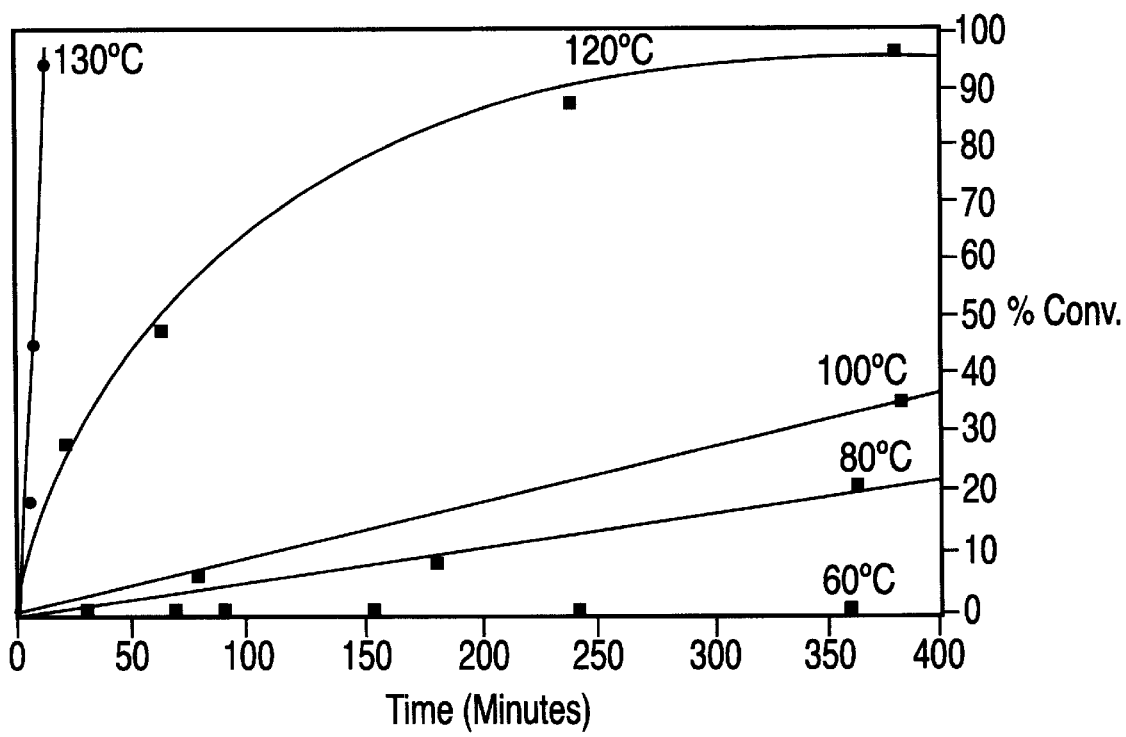
FIG. 8 is a stability plot of percent conversion vs. time at 60° C., 80° C., 100° C., 120° C. and 180° C.

These results illustrate that the nitrile oxide precursor reactivity drops off significantly at lower temperature. This is important in order to achieve a hot melt adhesive system with minimal reactivity at typical pot temperature. A summary of the results is shown in FIG. 8.

EXAMPLE 8

Infrared Spectroscopy

Figure 4:
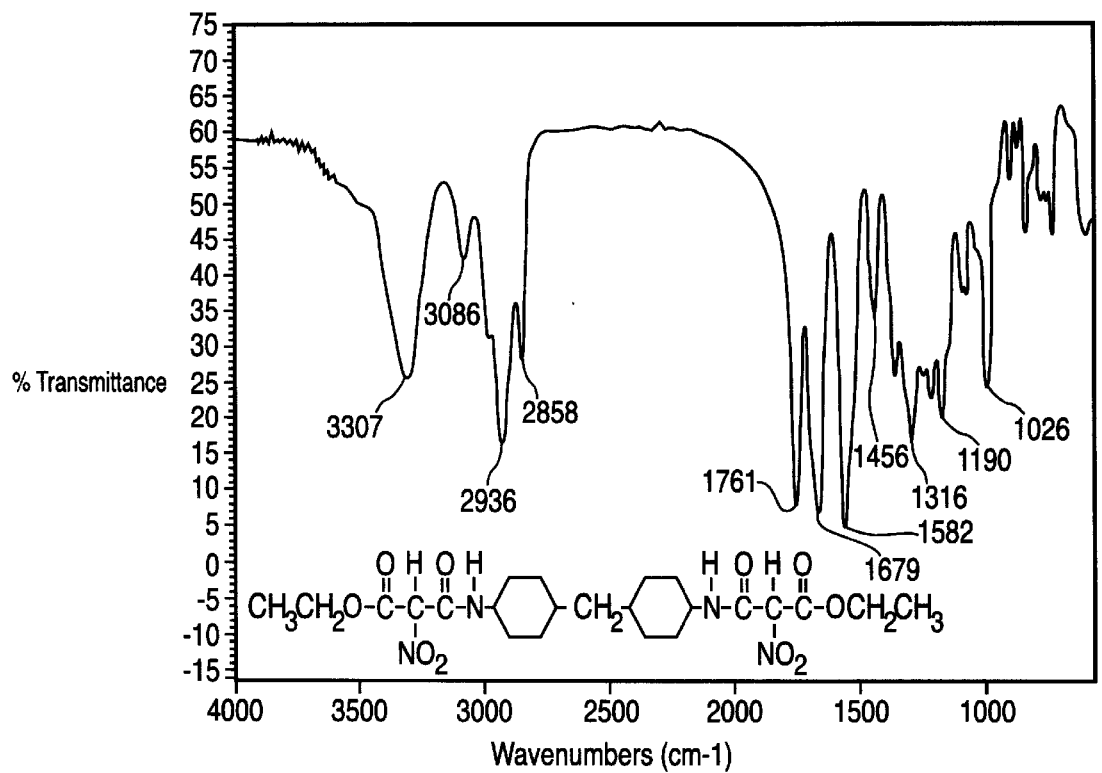
FIG. 4 is the Infrared Spectra ("IR") for a nitrile oxide precursor derived from DESMODUR W.

All of the nitrile oxide precursors made from isocyanates had very similar infrared spectra, see FIG. 4. The typical bonds or peaks found in the spectra which helped to confirm their preparation were; the amide NH (~3400 cm$^{-1}$), ester carbonyl (1760 cm$^{-1}$), amide carbonyl (1670 cm$^{-1}$), and the C—O stretch of the ester (1020 cm$^{-1}$).

When the nitrile oxide precursor was in the potassium salt form, the location of the carbonyls were at somewhat lower wave numbers (1700, 1630 cm$^{-1}$) while the C—O stretch was at a higher wave number (1090 cm$^{-1}$) than that found in the protonated version.

Reactions that used acid chlorides or sulfonyl chlorides in place of isocyanates as electrophiles, did not require protonation in the work-up to yield the final product since potassium chloride is eliminated, see Scheme 1.

Scheme 1
Precursor Formation from Acid Chloride

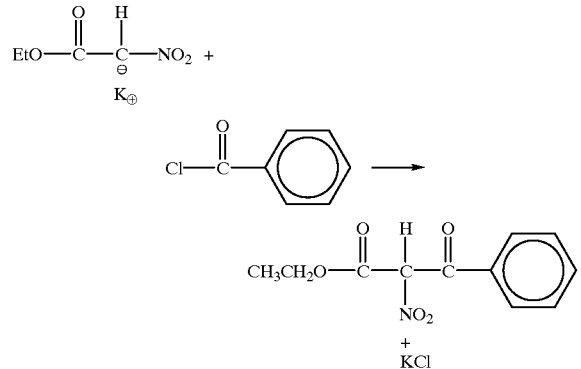

As the protonated product was formed directly in the reaction vessel the IR spectrum of reaction sample was identical to that of the product with no frequency shifts induced upon isolation.

As the protonated product was formed directly in the reaction vessel the IR spectrum of reaction sample was identical to that of the product with no frequency shifts induced upon isolation.

EXAMPLE 9

Differential Scanning Calorimetry (DSC)

Figure 5:
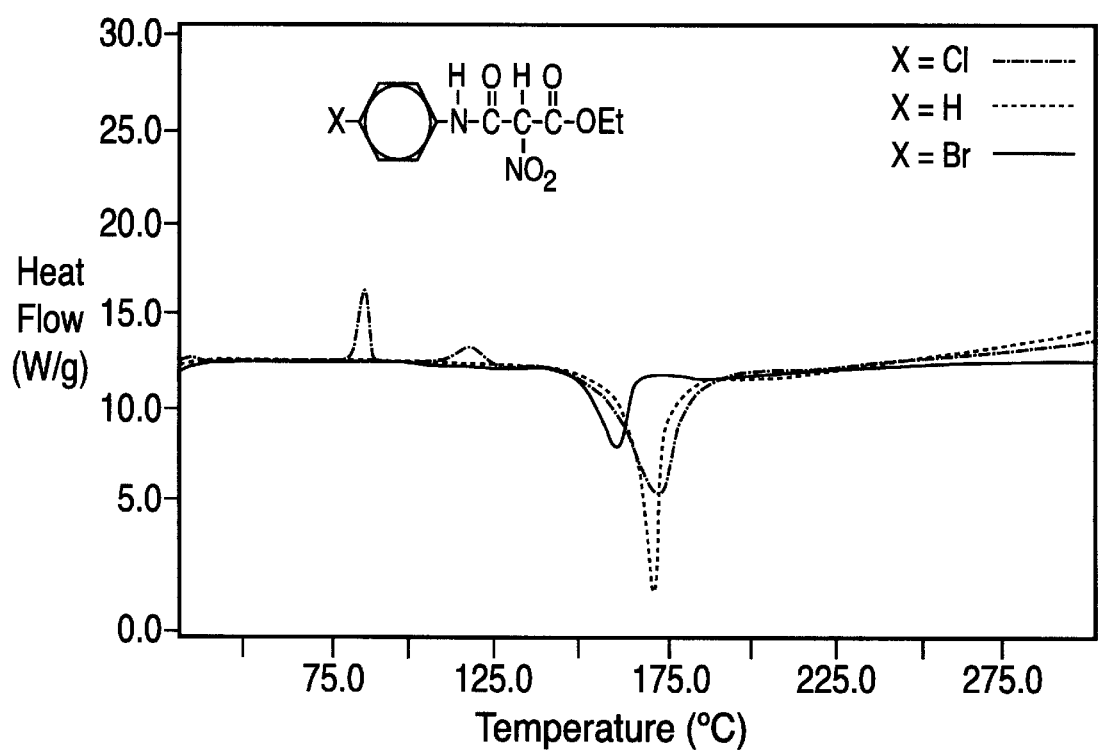
FIG. 5 is the differential scanning calorimetry ("DSC") of halogenated monofunctional aromatic nitrile oxide precursors.

The temperatures at which the nitrile oxide precursors melted and decomposed to the nitrile oxide were assessed by DSC. The melting point temperature ($T_m$) for most of the monofunctional nitrile oxide precursors was found to be lower than the decomposition temperature leading to the nitrile oxide (see FIG. 5). Also, the presence of additional functionality on the precursor (e.g., halides) generally caused the $T_m$ to shift to higher temperatures.

Figure 6:
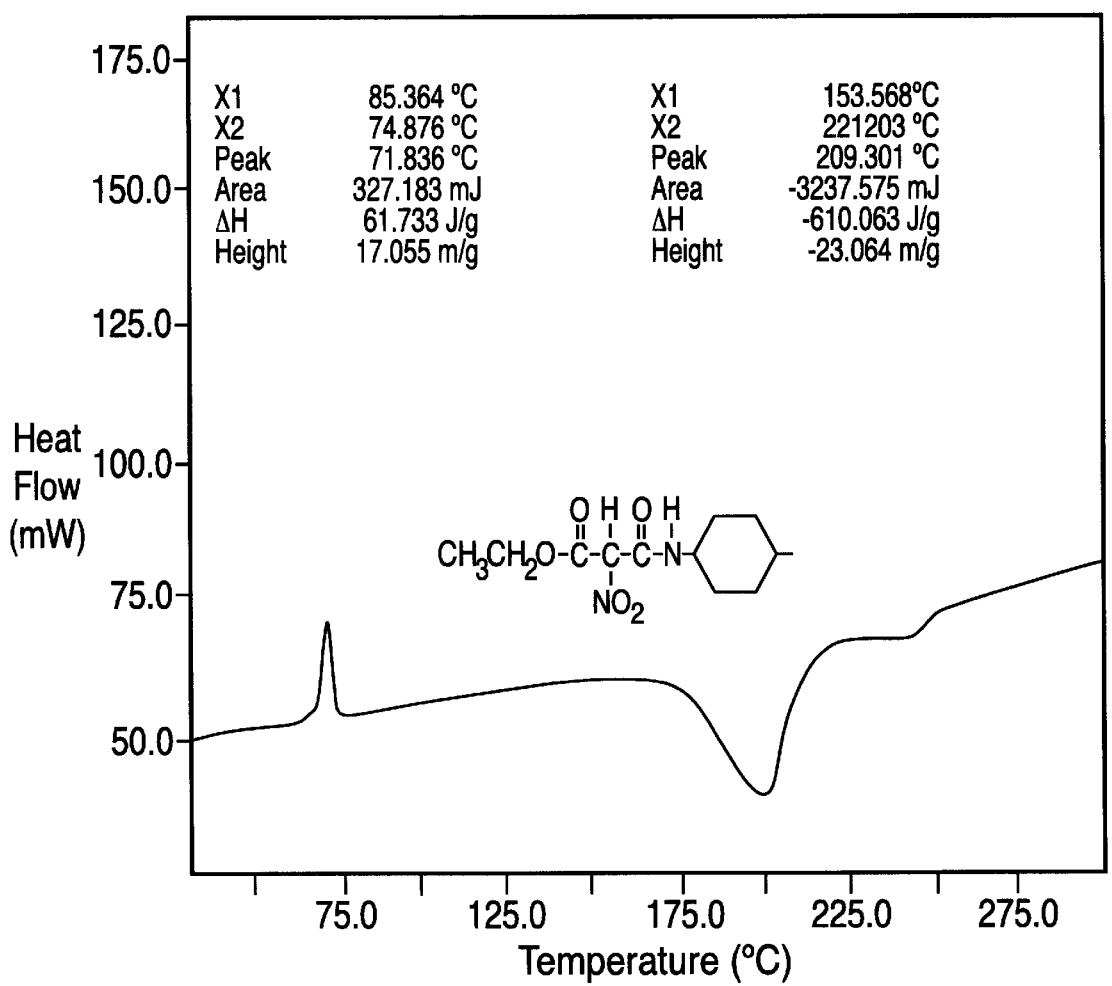
FIG. 6 is the DSC of monofunctional aliphatic nitrile oxide precursor derived from cyclohexylisocyanate.

Aliphatic nitrile oxide precursors showed a lower melt temperature and a higher decomposition temperature than the aromatic versions, as shown in FIG. 6. This higher decomposition temperature may prove to be very beneficial in controlling the reactivity of the adhesive systems.

Figure 7:
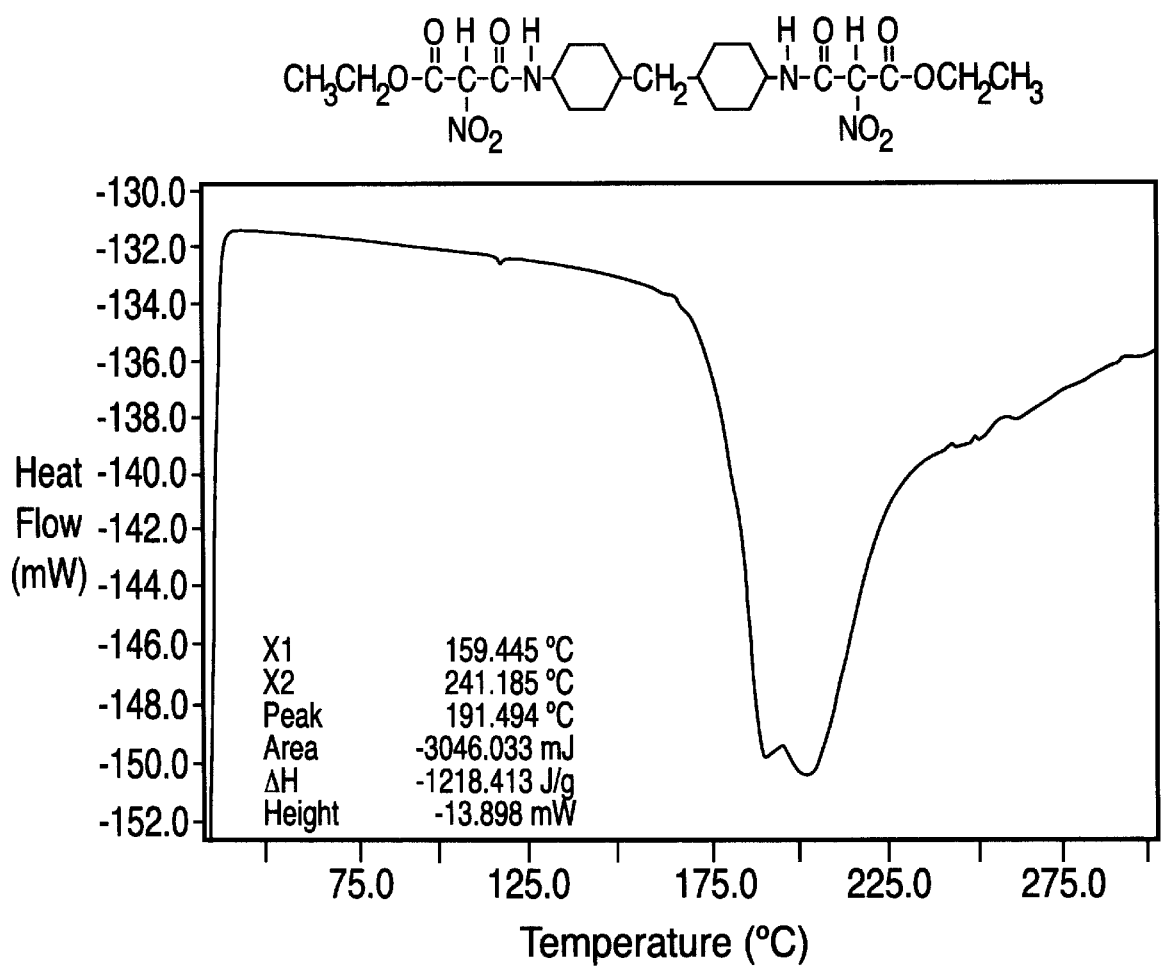
FIG. 7 is the DSC of a difunctional aliphatic nitrile oxide precursor derived from DESMODUR W.

The same trend between the melt and decomposition temperature was not observed in the difunctional aromatic nitrile oxide precursors (see FIG. 7). Here, it was observed that the melt temperature was the same or higher than the decomposition temperature.

EXAMPLE 10

Polymer Crosslink Studies by Rheometric Dynamic Analysis

Figure 9:
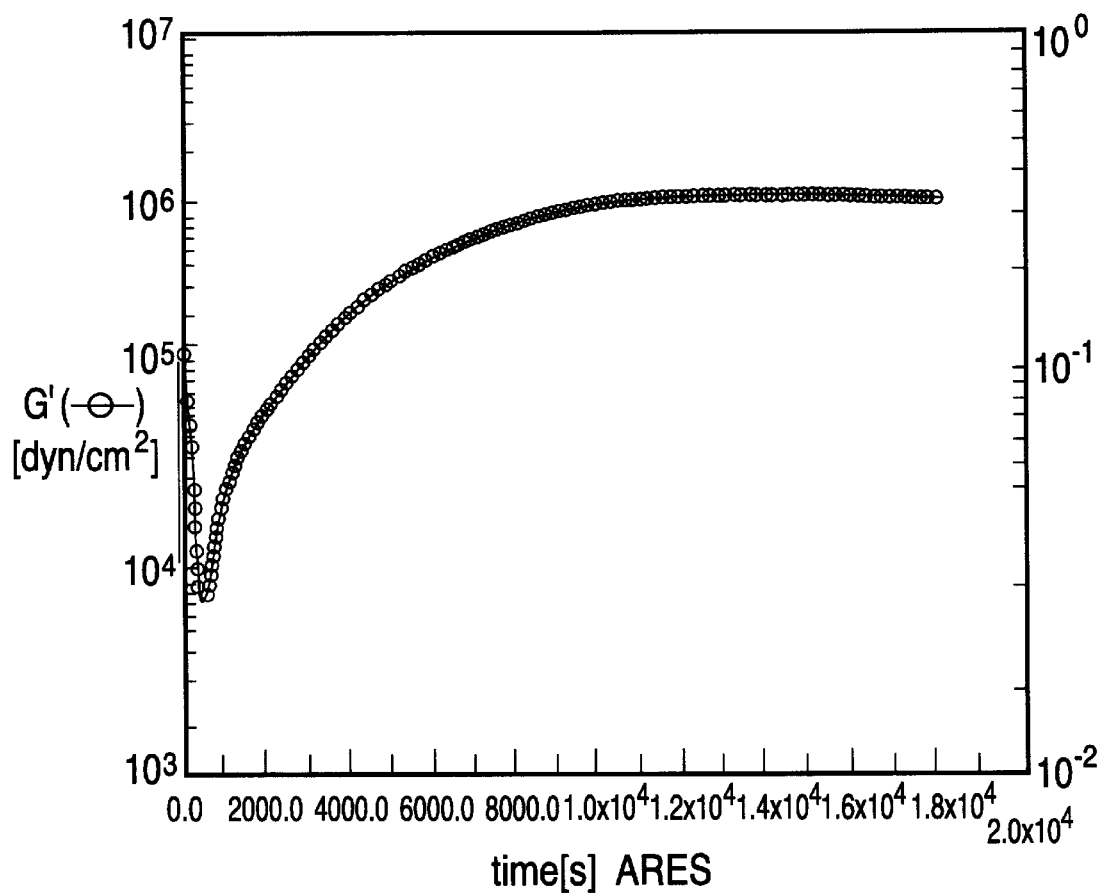
FIG. 9 is the RDA, ("rheometric dynamic analysis") plot of ISOLENE 400 in 10:1 molar ratio with difunctional nitrile oxide precursor at 150° C.
Figure 10:
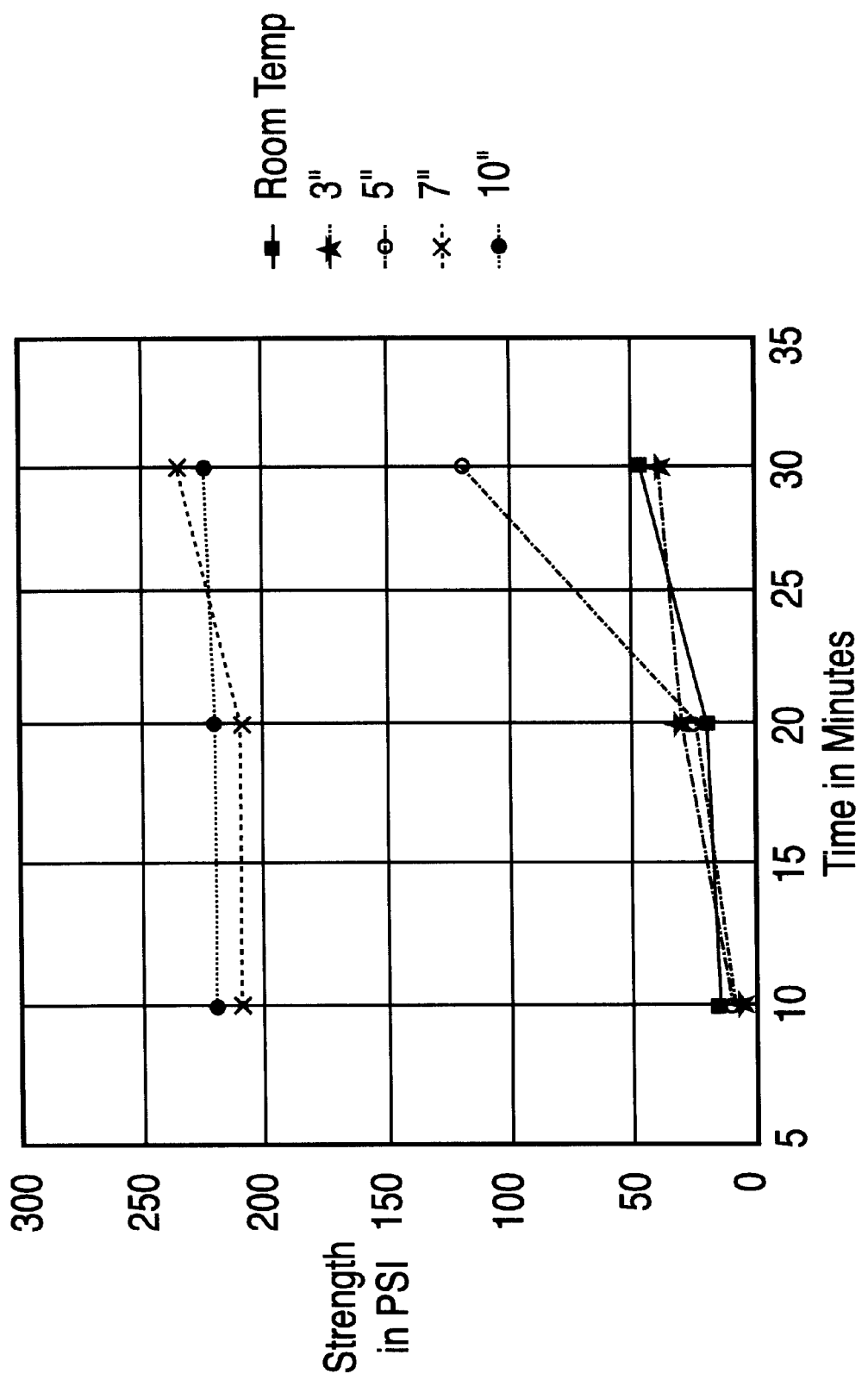
FIGS. 10–13 are plots of strength development as a function of time.
Figure 11:
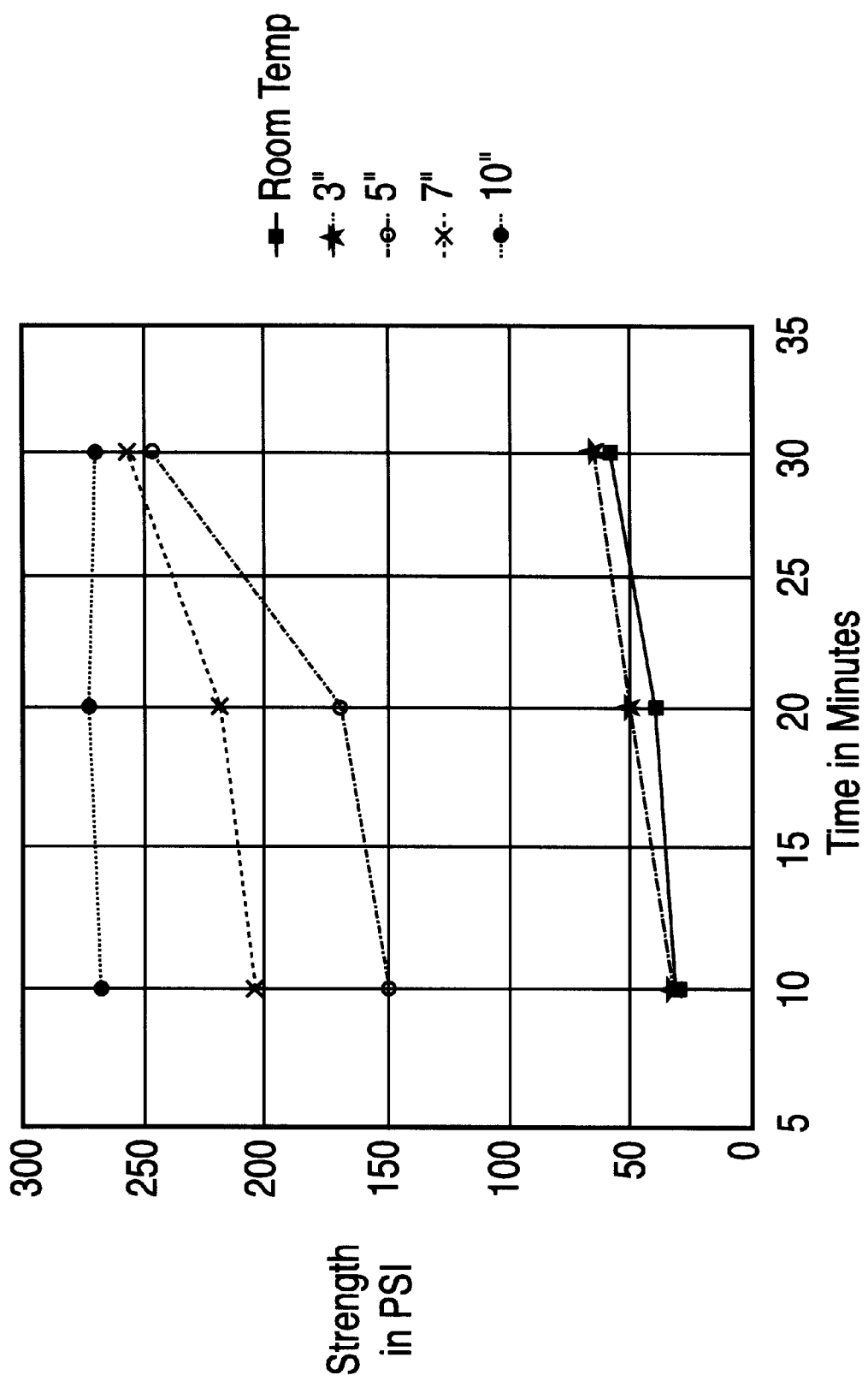
Figure 12:
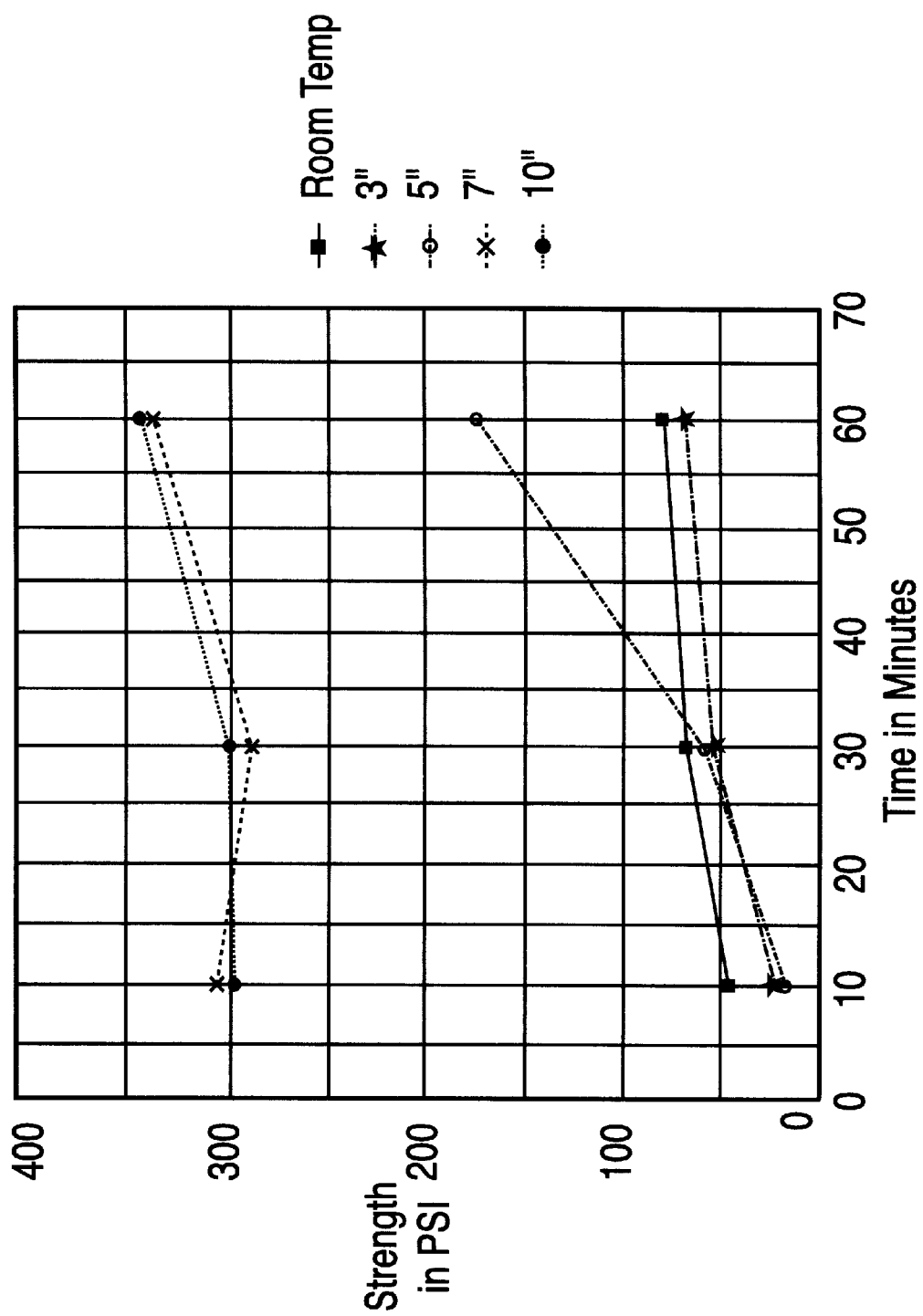
Figure 13:
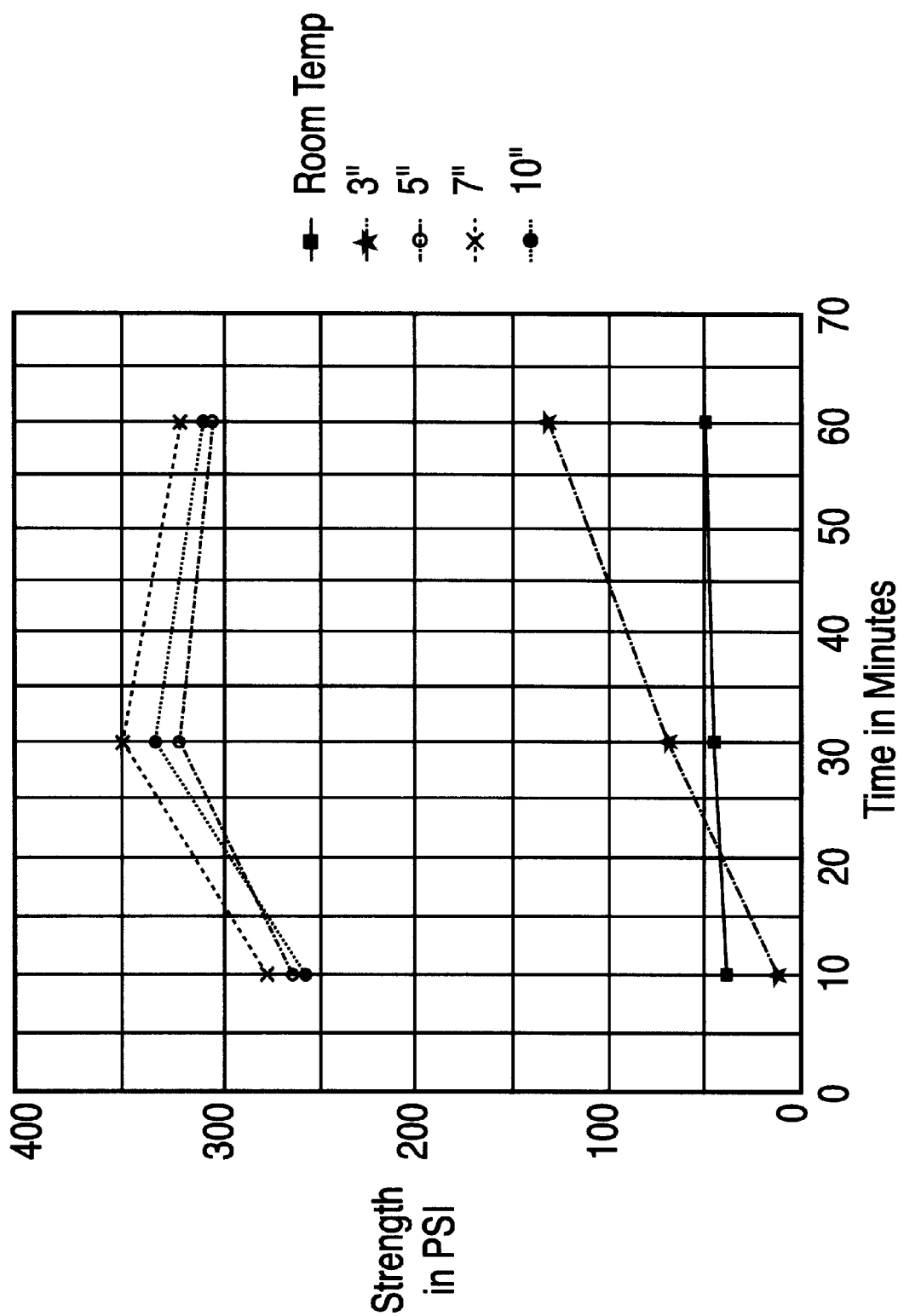

ISOLENE 400, an olefin polymer (0.499) available form Hardman Chemicals, was combined with a difunctional nitrile oxide precursor compound derived from DESMO-DUR W (hydrogenated MDI) (0.368 g) and heated with stirring in an oil bath to 70° C. until homogeneous. The mole ratio of olefin to nitrile oxide precursor is 10:1. A small portion of the formulation was placed between two RDA steel plates and subjected to a dynamic temperature ramp study using rheometric dynamic analysis. The temperature was increased 10° C./minute to 150° C. and held there for 5 hours. (See FIG. 9). A sample of the polymer without precursor compound was also tested, as a control, and no increase in modulus was observed. As seen in FIG. 9, the polymer with the nitrile oxide precursor crosslinking agent did increase in modulus fairly rapidly reaching the plateau value in 8,000 seconds.

EXAMPLE 11

In order to determine the reactivity of the precursor compounds with a polymer having pendant C≡N functionality, the reaction of the monofunctional aliphatic nitrile oxide precursor derived from cyclohexyl isocyanate was reacted with undecyl cyanide, using the method of Example 7 but replacing 1-dodecene with undecyl cyanide, and the resulting product was analyzed by HPLC and LC/MS. The LC/MS results show a peak bearing a mass ion of 350 corresponding to the molecular weight of the expected product indicating that the following reaction has occurred:

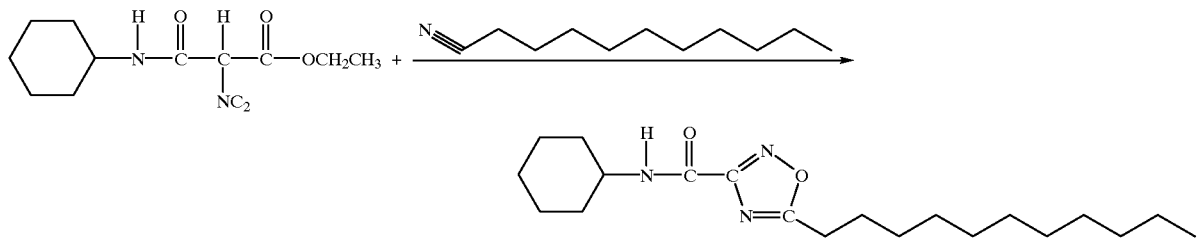

EXAMPLE 12

The procedure disclosed in Leslie-Smith, M. G., et al., Tet. Let. 1994, 35, 9251–9254 was repeated in an attempt to prepare a monofunctional aromatic nitrile oxide precursor. This example will show the low yields of aromatic nitrile oxide precursors.

In a closed vessel that was dried at 180° C. prior to set up and purged with nitrogen, 40 ml dry toluene, 4.54 g of anhydrous potassium carbonate and 4.0 g of phenyl isocyanate were stirred and heated to 60 to 65° C. Samples were withdrawn periodically and analyzed using infrared spectroscopy to detect the disappearance of isocyanate functionality. Reactions were complete once all isocyanate was consumed. The reference shown above indicated ~30% yield. When the procedure of the reference was repeated here, similar low yields, 20 to 30%, were obtained.

Infrared and 1H NMR spectroscopic analysis of the cured reaction mixture of this example indicated a significant formation of urea by-product (diphenyl urea) which results from the reaction of phenyl isocyanate with water. It is presumed that the water is generated in the process is likely the result of $KHCO_3$ disproportionation.

EXAMPLE 13

Nitrile oxide precursors were prepared by the method disclosed in Leslie-Smith, M. G., et al., Tet. Let. 1994, 35, 9251–92540. This method involves the generation of potassium enolate of ethyl nitroacetate in situ using $K_2CO_3$ in toluene as the solvent.

This example will show the incomplete reaction of difunctional aromatic isocyanates in the method of the reference.

In a closed vessel that was dried at 180° C. prior to set up and purged with nitrogen, 4.40 g of ethyl nitroacetate, 40 ml dry toluene, 4.54 g of anhydrous potassium carbonate and 2.64 g of phenylene diisocyanate were stirred and heated to 60 to 65° C. Samples were withdrawn periodically and analyzed using infrared spectroscopy to detect the disappearance of isocyanate functionality. Reactions were complete once all isocyanate was consumed. However, in this example, using the method of Leslie-Smith, the level of isocyanate was never depleted (14 days) and therefore it was not possible to prepare the salt form of the difunctional nitrile oxide precursor compound (0% yield).

EXAMPLE 14

The procedure of Leslie-Smith, M. G., et al., Tet. Let. 1994, 35, 9251–9254, as described in Example 12 herein, was repeated using cyclohexyl isocyanate, an aliphatic isocyanate as the electrophile instead of phenyl isocyanate. No desired reaction product was obtained, as evidenced by IR spectroscopy which shows no consumption of the NCO peak at 2250 $cm^{-1}$ after 6 days at 65° C. These results indicate that it is not possible to isolate an aliphatic nitrile oxide precursor using the procedure disclosed in the Leslie-Smith reference, possibly due to the low reactivity of the aliphatic isocyanate in the alkylation step which doesn't react at all under Leslie-Smith conditions.

EXAMPLE 15

This example shows the lack of compatibility of the difunctional aromatic nitrile oxide precursor derived from PPDI with non-polar olefins as evidenced by the lack of adduct formation.

In a 2 dram vial were mixed 0.1 grams of the precursor derived from p-phenylene diisocyanate, ("PPDI"), prepared according to Example 1, and 5.0 grams 1-dodecene, and immersed into a 120° C. oil bath while stirring. Samples were withdrawn periodically for analysis by HPLC, which indicated no adduct formation. This lack of reaction may be due to poor solubility of the aromatic precursor in all but a few solvents. In 1-dodecene, phase separation is observed which may result in dimerization of the formed nitrile oxide.

EXAMPLE 16

This examples shows the compatibility of difunctional aliphatic nitrile oxide precursors compounds and non-polar olefins. For example, when the precursor derived from isophorone diisocyanate was reacted with 1-dodecene adduct formation was found to occur.

In a 2 dram vial were mixed 0.1 grams of the precursor derived from isophorone diisocyanate, prepared according to Example 1, and 5.0 grams 1-dodecene, and immersed into a 120° C. oil bath while stirring. Samples were withdrawn periodically for analysis by HPLC, which indicated adduct formation. These results were also confirmed by LC/MS.

EXAMPLE 17

This example shows how certain polar solvents cause aromatic precursors to revert back to isocyanate. The reaction was examined by reacting monofunctional aromatic nitrile oxide precursor derived from phenyl isocyanate (0.1 g) with 1-dodecene (6.6 g) in the presence of triglyme (13.2 g) at 120° C. When the final reaction mixture was analyzed by HPLC, using an aqueous mobile phase, no adduct formation was detected. Instead, a component, that was later confirmed by LC/MS to be diphenyl urea, was observed (FW 212.2). The final reaction mixture was also analyzed by GS/MS where phenyl isocyanate (FW 119.1) was observed, but no adduct could be detected.

EXAMPLE 18

Polar solvents can be used with aliphatic nitrile oxide precursors without reversion occurring. For the desired application it is necessary for the nitrile oxide precursor to be soluble in the formulation, and not revert back to isocyanate upon heating. These criteria are best met with aliphatic nitrile oxide precursors. This was not the case with systems as shown in Example 17. This is a significant finding. While hot melt systems typically do not contain solvent, they can often be comprised of polyether components with similar polar ether functionality as found in triglyme. It is therefore anticipated that similar reactivities for the nitrile oxide precursors would be obtained in polyether based hot melt adhesives.

For instance, crosslinking of the nitrile oxide precursor derived from isophorone diisocyanate ("IPDI") and DESMODUR W with 1-dodecene in the presence of triglyme was performed. The mass spectra of the difunctional adducts prepared clearly indicate the expected DESMODUR W precursor/1-dodecane adduct MW of 684.5 and the IPDI precursor/1-dodecane adduct MW of 644.5 resulting from difunctional adduct formation.

EXAMPLE 19

Pot Stability

A PUR reactive hot melt that had 2.5% free isocyanate was reacted with allyl alcohol to generate an allyl capped reactive hot melt. This allyl capped reactive hot melt (5.0 g) was mixed with (0.12 g) nitrile oxide precursor derived from DESMODUR W. This mixture was placed between two parallel plates and heated at 100° C. The viscosity was measured over several hours utilizing Rheometric Dynamic Analysis (RDA). A very minimal increase in viscosity (2.5% per hour) occurred at 100° C. This indicates that good pot stability is achieved at 100° C. The desired pot stability should be less than 20% per hour.

EXAMPLE 20

Table III illustrates the adhesive compositions used in this example.

TABLE III

|  | A | B | C | D |
|---|---|---|---|---|
| Modaflow | 0.2 | 0.2 | 0.2 | 0.2 |
| PPG | 40.9 | 40.9 | 38.8 | 38.8 |
| butadiene polymer | 2.2 | 2.2 | 4.3 | 4.3 |
| methacrylate copolymer | 25.0 | 25.0 | 25.0 | 25.0 |
| polyesterdiol | 18.5 | 18.5 | 18.5 | 18.5 |
| catalyst | 0.1 | 0.1 | 0.1 | 0.1 |
| MDI | 14.0 | 14.0 | 14.7 | 14.7 |
| nitrile oxide precursor | — | 0.5 | — | 1.0 |
| % NCO | 2.1 | 1.9 | 2.3 | 1.8 |
| Viscosity | 4,600 | 5,525 | 5,100 | 12,400 |
| Stability | 4.2 | 6.3 | 4.2 | 24.2 |

The methacrylate copolymer used was ELVACITE 2013 which is a 64% butyl methacrylate and 36% methyl methacrylate copolymer of I.V. 0.2 available from ICI. The ELVACITE was vacuum dried in a dessicator for 24 hours immediately prior to use herein.

The polypropylene glycol used was PPG 2025 which is a polyproylene glycol polyether diol with 2,000 molecular weight from Acro Chemical.

The butadiene polymer used was R45HT which is a liquid, hydroxyl terminated homopolymer of butadiene with molecular weight 2,800 available from Atochem Inc.

The polyester diol used was DYNACOLL 7360, a polyester diol of 1,6 hexanediol adipate with 3,500 molecular weight from Creanova Inc.

The catalyst was 2,2'dimorpholinodiethylether, TEXCAT DMDEE available from Texaco.

The dinitrile precursor compound was derived from DESMODUR W.

The following procedure was used. The polyols and ELVACITE 2013 were added to the vessel and heated to 100° C. until ELVACITE was dissolved. The methylene bisphenyl diisocyanate, MDI, was added, and the reaction allowed to proceed for 3 hours. The difunctional nitrile oxide precursor was added into the vessel and stirred for 20 minutes. The reaction contents were poured hot from the vessels. The % NCO and viscosity of samples were determined and reported in Table III.

Samples A and C, which do not contain nitrile oxide precursor had lower viscosities than the samples containing the precursor compounds of the present invention.

EXAMPLE 21

Each of samples A, B, C, D, prepared according to Example 20, were dispensed on an HPL substrate with 10-mil glass bead serving as a spacer to prepare lap shear specimen. Lap shear samples were clamped with clips and put in an oven at 350° F. for 3, 5, 7, and 10 minutes. After removal from the oven, the samples were pulled at ambient temperature after 10, 20, and 30 minutes, respectively. The results are shown in FIGS. 10 to 13.

The results indicate that samples B and D containing dinitrile precursor compounds of the present invention had good strength after 5 minutes at 350° C. The controls, samples A and C, which did not contain the precursor compound required an additional 2 minutes in order to reach good bond strength.

1. A compound of the formula
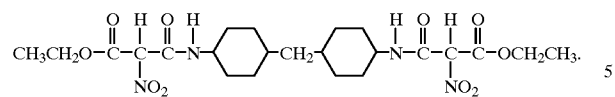

We claim: